United States Patent [19]

Braithwaite

[11] Patent Number: 5,778,873
[45] Date of Patent: Jul. 14, 1998

[54] METERING DEVICE FOR USE IN TRANSFERRING A DESIRED VOLUMETRIC DOSE OF A FLOWABLE SUBSTANCE FROM A STORAGE CONTAINER

[75] Inventor: Philip W. Braithwaite, Strensham, United Kingdom

[73] Assignee: Innovata Biomed Limited, St. Albans, United Kingdom

[21] Appl. No.: 284,522

[22] PCT Filed: Feb. 18, 1993

[86] PCT No.: PCT/GB93/00335

§ 371 Date: Oct. 12, 1994

§ 102(e) Date: Oct. 12, 1994

[87] PCT Pub. No.: WO93/16748

PCT Pub. Date: Sep. 2, 1993

[30] Foreign Application Priority Data

Feb. 21, 1992 [GB] United Kingdom ............. 9203761

[51] Int. Cl.$^6$ ............. A61M 15/00; A61M 16/00; B05D 7/14; B65D 83/06
[52] U.S. Cl. ............. 128/203.15; 128/203.19
[58] Field of Search ............. 128/203.15, 203.12, 128/200.14, 203.23, 203.28, 203.29, 203.19, 203.21, 203.25, 200.24

[56] References Cited

U.S. PATENT DOCUMENTS

| | | | |
|---|---|---|---|
| 1,858,735 | 5/1932 | Goodsell | 128/203.15 |
| 2,587,215 | 2/1952 | Priestly | 128/203.15 |
| 4,604,847 | 8/1986 | Moulding, Jr. et al. | 128/203.15 |
| 4,635,829 | 1/1987 | Brittingham | 222/278 |
| 4,934,358 | 6/1990 | Nilsson et al. | 128/200.23 |
| 5,447,151 | 9/1995 | Bruna et al. | 128/203.15 |

FOREIGN PATENT DOCUMENTS

| | | | |
|---|---|---|---|
| 0079478 | 5/1983 | European Pat. Off. | |
| 0166294 | 1/1986 | European Pat. Off. | |
| 0424790 | 5/1991 | European Pat. Off. | |
| 0448204 | 9/1991 | European Pat. Off. | |
| 2516387 | 5/1983 | France | |
| 1498398 | 1/1969 | Germany | |
| 3243731 | 5/1984 | Germany | |
| 2165159 | 4/1986 | United Kingdom | 128/203.15 |
| 2178965 | 2/1987 | United Kingdom | 128/203.15 |
| 2248400 | 4/1992 | United Kingdom | 128/203.15 |
| 9200771 | 1/1992 | WIPO | |
| 9204928 | 4/1992 | WIPO | 128/203.15 |
| 9209322 | 6/1992 | WIPO | 128/203.15 |
| 9218188 | 10/1992 | WIPO | 128/203.15 |

*Primary Examiner*—Kimberly L. Asher
*Attorney, Agent, or Firm*—Edwin D. Schindler

[57] ABSTRACT

A metering device, for use in transferring a desired volumetric dose of a flowable substance from a storage chamber containing the flowable substance to a location outside the storage chamber, is disclosed. An outlet conduit is arranged between the storage chamber and the location to which the dose is to be transferred. The metering device is of such size and shape as to be able to pass through the outlet conduit and includes first and second end element which, when the metering device is located inside the outlet conduit, are in a sealing engagement with the inner walls of the outlet conduit. The shape of the metering device between the first and second end elements is such that a space of the desired dose volume is defined between the first and second end elements and the intervening section of the inner walls of the outlet conduit, in which space the flowable substance from the storage chamber may be enclosed. The metering device is of particular use in a dry powder inhaler.

37 Claims, 15 Drawing Sheets

FIG. 5
FIG. 6
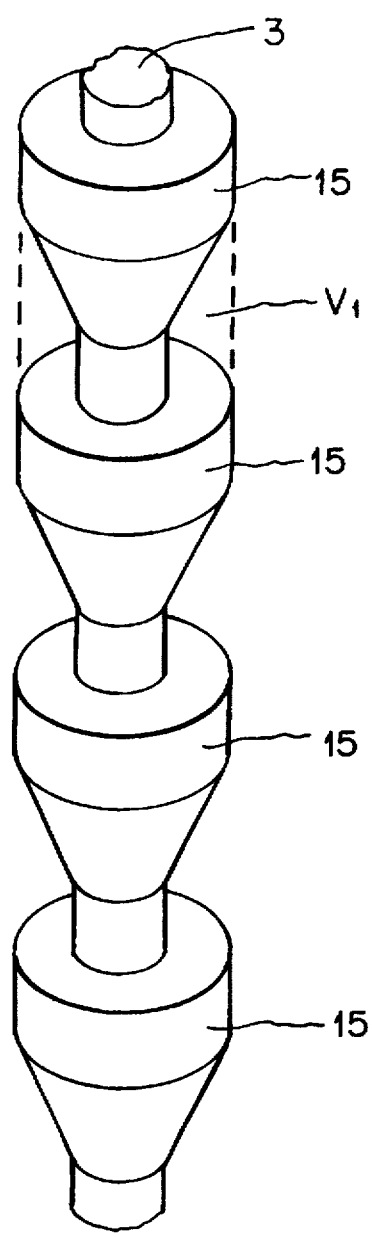
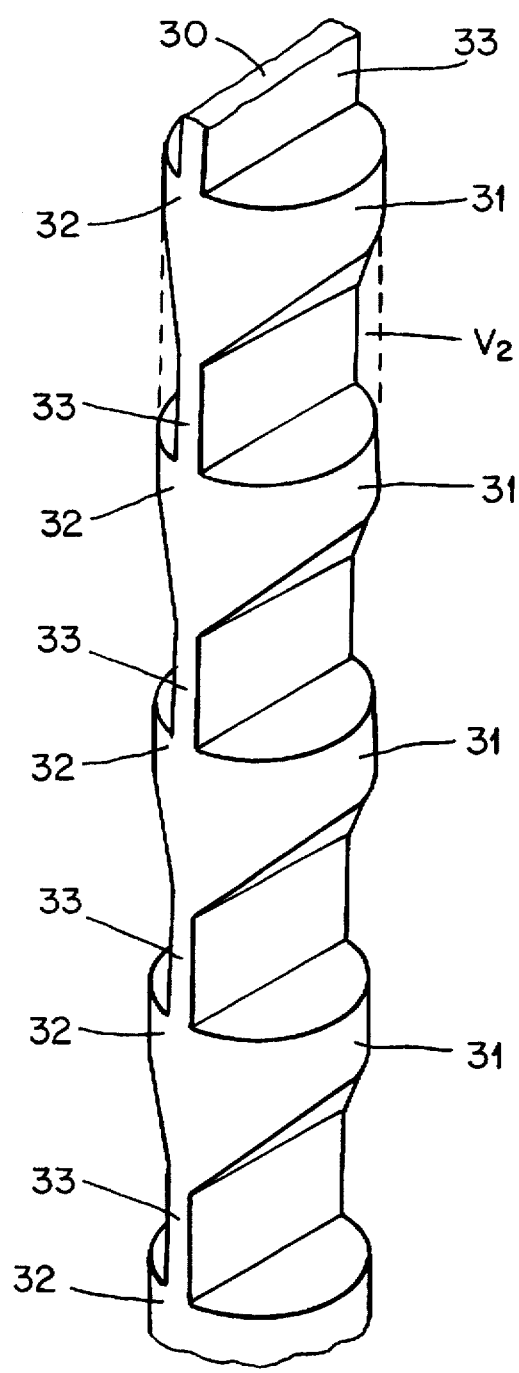

AIR FLOW

AIR FLOW

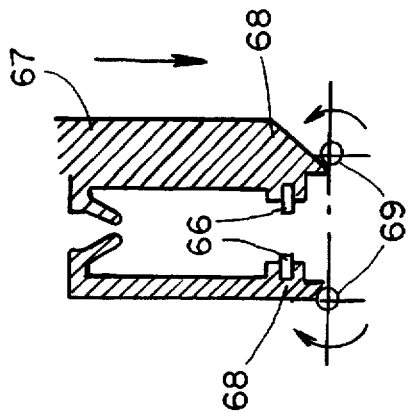
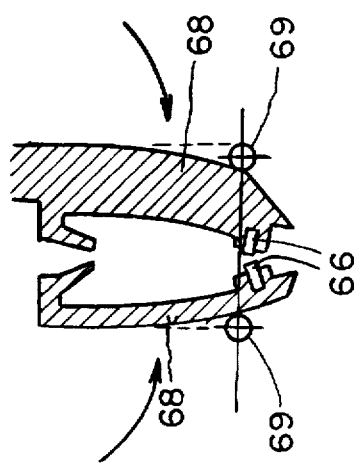
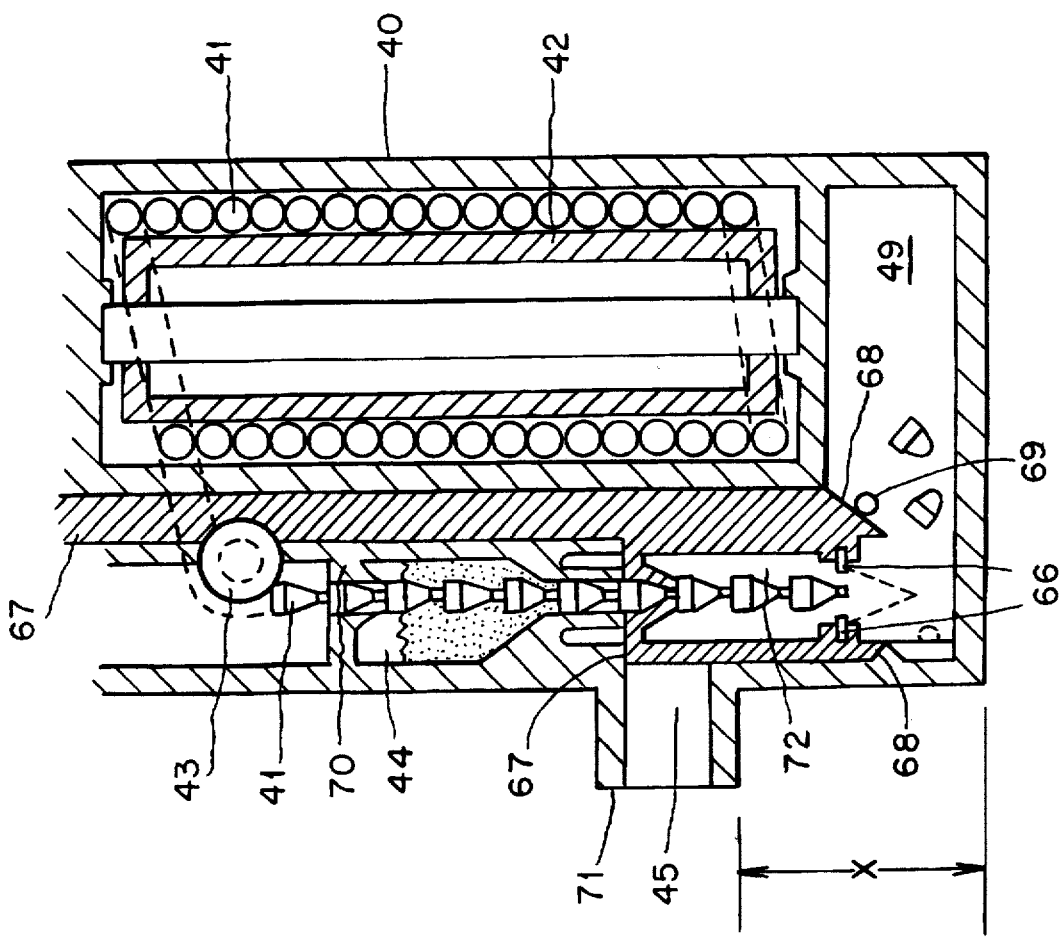

even greater. So that this build-up of adherent powder, in many of the inhalers previously proposed.
METERING DEVICE FOR USE IN TRANSFERRING A DESIRED VOLUMETRIC DOSE OF A FLOWABLE SUBSTANCE FROM A STORAGE CONTAINER This application is a 371 of PCT/GB93/00335 filed Feb. 18, 1993.

FIELD OF THE INVENTION

This invention relates to a metering device for transferring a desired volumetric dose of a flowable substance from a storage chamber containing the substance to a location outside the chamber, which device is of particular use in an inhaler for delivering a dose of a medicament or other substance for inhalation into the lungs of a user. The invention also relates, inter alia, to an inhaler incorporating such a metering device; to a method for transferring a desired volumetric dose of a substance from one location to another using such a device; and to a container for containing metered doses of a substance, the container incorporating one or more such devices.

BACKGROUND OF THE INVENTION

It is often necessary to transfer an accurate volume of a substance from a storage chamber containing that substance to another location, but it is not always easy to effect the transfer accurately and efficiently. In particular, it is often desired to transfer a powdered medicament from a storage chamber to an inhalation passage in a dry powder inhaler.

Powder inhalers, which deliver a drug in a dry, finely divided form, have been shown to give certain medical advantages over other forms of delivery system. In particular, they are more popular than inhalers which propel a drug in pressurised gas from an aerosol, because of environmental and other considerations.

EP-079478, EP-166294 and GB-2165159 disclose examples of dry powder inhalers which include a medicament storage chamber and an inhalation passage through which air is drawn via a mouthpiece. A metering member provided with a metering recess takes a dose of medicament from the storage chamber and deposits it in the inhalation passage.

It is considered that the accuracy of such arrangements can be very poor: on the one hand, by repeated indexing of the metering member it is possible to deposit two or more doses of medicament into the inhalation passage, resulting in the administration to the user of an overdose of medicament; on the other hand, since the medicament normally drops from the metering recess into the inhalation passage under gravity, particles of medicament can adhere to the interior of the metering recess so that an underdose is delivered.

US-2587215 discloses dry powder inhalers with the same disadvantages as those mentioned above. However, this document also discloses an embodiment in which the metering member presents the medicament in an upwardly open dispensing cup to a mixing chamber, where it is mixed with air before being sucked into an inhalation tube via a nozzle having a narrow opening. Air sucked into the inhaler passes into the inhalation tube either directly or through the mixing chamber and nozzle. Accordingly, not all the air passes over the dispensing cup. If medicament adheres to the surface of the dispensing cup but is not sucked therefrom, an underdose of medicament will be delivered to the user. Upon repeated use of a dispensing cup to deliver doses to the inhalation tube, a continually increasing amount of the medicament powder can adhere to the base of the dispensing cup, resulting in progressively decreased dosages to the user.

This build-up of adherent powder is thought to be a source of inaccurate dosing in many of the inhalers previously proposed.

Moreover, in the inhaler of US-2587215, the metering member is a rotary sliding device journalised on a cylindrical pivot member extending from the bottom of the body of the device. Such an arrangement is susceptible to jamming due to ingress of powdered medicament between the cylindrical contacting surfaces of the pivot member and the metering member.

Another form of inhaler which is currently available includes a metering member having a number of tapered metering recesses which are open at top and bottom. In use, finely divided medicament from a storage chamber is packed into the recesses, whereupon the metering member is moved to a dispensing position in which air can be drawn through the recesses to draw out the medicament. This device is considered to have a number of major shortcomings. Firstly, the metering recesses are prone to clogging. Secondly, a large amount of suction is required, so that the device is unsuitable for use by patients with breathing problems. Thirdly, two hands are required to operate the device.

An improvement over the above described inhalers is described in our earlier PCT patent application, No. PCT/GB91/01147. This discloses an inhaler in which the metering member comprises at least one dispensing cup which, when filled from a storage chamber with a dose of the substance to be delivered, is presented to the inhalation passage in an upwardly open position. The substance to be delivered is removed from the dispensing cup, rather than by the action of gravity, by air flow through the inhalation passage. Thus, in normal use of the inhaler, repeated indexing of the metering member should not result in multiple doses of the substance being delivered into the inhalation passage.

The inhaler described in PCT/GB91/01147 incorporates means for ensuring that the dispensing cup is substantially free from the substance to be delivered, before it is presented to the storage chamber to be re-filled with the substance. This means may comprise a specially shaped inhalation passage; means for moving the dispensing cup into a downwardly open position after it has been presented to the inhalation passage and before it is re-presented to the storage chamber; or means, such as resilient wiping means, for dislodging any remaining substance from the cup after it has been presented to the inhalation passage. In all cases, at least one of these special means must be included in the inhaler so as to prevent any of the substance from remaining in the dispensing cup after it has been presented to the inhalation passage. If any of the substance did remain, this could affect accuracy when the dispensing cup was refilled from the storage chamber ready for subsequent representation to the inhalation passage.

The need to ensure that a metering member is substantially free from the substance to be delivered, after each presentation to the inhalation passage of an inhaler, arises largely from the fact that the metering member is constantly being re-presented to the storage chamber, re-filled with the substance and returned to the inhalation passage. The metering member is required to deliver an accurate dose of the substance each time it passes through the inhalation passage.

It is an aim of the present invention to provide improved means for accurately transferring a dose of a substance, such as a powdered drug, from one location to another, which means may be used, inter alia, in an inhaler to transfer a dose of drug from a storage chamber to an inhalation passage. An inhaler incorporating such means should overcome or at least mitigate the above described problems associated with conventional inhalers, and should be capable of delivering an accurate dose of drug to a user each time it is used.

STATEMENTS OF THE INVENTION

According to a first aspect of the present invention there is provided a metering device for use in transferring a desired volumetric dose of a flowable substance from a storage chamber containing the substance to an outlet conduit communicating with the chamber, the device being of such dimensions as to be able to pass into the outlet conduit and having first and second end elements which, when the metering device is located inside the conduit in use, are in sealing engagement with the inner walls of the conduit, the shape of the metering device between the first and second end elements being such that a space of the desired dose volume is defined between the first and second end elements and the intervening section of the inner walls of the conduit, in which space substance from the storage chamber may be enclosed when the metering device has passed out of the storage chamber into the outlet conduit in use.

The flowable substance may be a pulverulent material, for example a powdered drug.

Such a device allows the relatively simple and efficient transfer of precise volumetric doses of a substance from one location to another. Movement of the device from the storage chamber, through the outlet conduit, to another location causes the device to carry with it as it moves a precisely defined dose of substance, trapped between the first and second end elements of the device and the inner walls of the conduit. When the device exits the outlet conduit, the substance can then be released ready for use as desired.

The metering device need not be large in size, complex in shape or cumbersome. In use, several such devices may be moved through the outlet conduit to transfer several successive doses of the substance. These factors mean that the device is of particular use in an inhaler, for transferring a powdered drug from its storage chamber to the inhalation passage of the inhaler. The device may also be used, however, to transfer a substance (eg, a powdered drug) from a storage chamber into a receptacle which is to be used to store and transport a measured amount of the substance for subsequent use in, for example, an inhaler.

According to a second aspect of the invention there is provided a metering device in accordance with the first aspect, in combination with a storage chamber for containing a substance of which a volumetric dose is to be transferred from the chamber, and an outlet conduit communicating with the chamber, the shape and dimensions of the device relative to those of the outlet conduit being as described in accordance with the first aspect of the invention.

The storage chamber may be part of an inhaler for delivering a substance to a user in a finely divided form, the chamber being for storing a quantity of that substance, and the outlet conduit then communicating between the chamber and an inhalation passage in the inhaler.

Thus, according to a third aspect of the present invention, there is provided an inhaler for delivering a substance in a finely divided form, the inhaler comprising a storage chamber for storing a quantity of the substance to be delivered; air intake means by which air may be drawn into the inhaler from the atmosphere; an inhalation passage communicating with the air intake means, through which passage air may be drawn using the air intake means; a storage chamber outlet conduit communicating between the storage chamber and the inhalation passage; a metering device in accordance with the first aspect of the invention for use in transferring a desired volumetric dose of the substance from the storage chamber to the inhalation passage via the outlet conduit, the metering device being movable through the outlet conduit from a first position, in which it is presented to the storage chamber to receive the substance, to a second position in which the desired volumetric dose of the substance is presented with the metering device to the inhalation passage; and indexing means operable to move the metering device from its first to its second position. The shape and dimensions of the metering device relative to those of the outlet conduit are as described in accordance with the first aspect of the invention.

The metering device may comprise a body in the form of a spool which may be located in, and preferably pass through, the outlet conduit in use. The device may also be one of a plurality of such devices arranged in series, which devices are able to pass through the storage chamber and into the outlet conduit in series so as to transfer a succession of metered doses of substance out of the storage chamber. In this case, the first end element of one device in the series may also serve as the second end element of the preceding device in the series, such that the desired volume is defined between two successive end elements as successive devices in the series pass into the outlet conduit in use.

The invention thus also provides, according to a fourth aspect, a plurality of metering devices arranged in series, each device being in accordance with the first aspect of the invention. The devices may be releasably or permanently attached to one another so as to be in a chain-like conformation, preferably a flexible or semi-flexible chain. The design of metering devices in accordance with the invention makes such flexibility possible.

A series of metering devices in accordance with the fourth aspect of the invention is ideal for use in an inhaler, because it allows sequential presentation of doses of a substance to the inhalation passage of the inhaler as the series is indexed through the inhaler. If the series is in the form of a flexible chain, it can then be rolled or folded up for compact storage in the inhaler. The series may be of any appropriate length. It may, for instance, be supplied in a length greater than might be needed for use in an inhaler, but capable of being broken up into usable lengths.

An inhaler in accordance with the third aspect of the invention thus preferably comprises a plurality of metering devices arranged in a series, in accordance with the fourth aspect of the invention, the series being movable as a series through the inhaler by means of the indexing means such that each metering device in the series may be moved via the outlet conduit from a first position, in which it is presented to the storage chamber to receive the substance, to a second position in which a desired volumetric dose of the substance has been transferred with that device to the inhalation passage.

So long as there is a sufficient number of metering devices in the series, a large number of doses can be delivered to the user without any particular metering device necessarily being re-presented to the storage chamber after it has reached the inhalation passage. A flexible chain in accordance with the invention is able to comprise a large number of devices without assuming undue amounts of space in an inhaler. The indexing means of an inhaler in accordance with the third aspect of the invention is thus preferably operable to move the metering device, or each device in a series included in the inhaler, away from the inhalation passage after it has reached its second position, in such a manner that the metering device is not re-presented to the storage chamber after having reached its second position.

In use of such an inhaler, the metering device moves, via the outlet conduit, from the storage chamber to the inhalation passage, where it delivers a volumetric dose of the substance, and thence to waste. It is not subsequently re-presented to the storage chamber to be filled with a further dose of the substance.

Since the metering device is not re-used, i.e. not used to deliver more than one dose of the substance to the inhalation passage, there is no need to incorporate in the inhaler means for ensuring that the metering device is substantially free from the substance after its presentation to the inhalation passage.

The inhaler preferably additionally comprises a waste chamber, in which the metering device may be housed after having been moved, by the indexing means, away from the inhalation passage.

Where the inhaler comprises a plurality of metering devices arranged in a series, operation of the indexing means preferably moves the series forward through the inhaler by the length of a fixed number of (typically one) metering devices, or of intervals between successive devices in the series, for each operation. Each metering device would thus pass in turn from its first to its second position, i.e. from the storage chamber to the inhalation passage, and preferably subsequently away from the inhalation passage and to a waste chamber. On passing from its first to its second position via the outlet conduit, each device would transfer to the inhalation passage a dose of substance, trapped between its first and second end elements and the inner walls of the outlet conduit as the device passes through the conduit.

The inhaler preferably comprises a number of metering devices which is either equal to or greater than the number of volumetric doses, of the substance to be delivered, which the storage chamber of the inhaler is adapted to hold. Thus, a large number of consecutive doses of the substance can be delivered to a user, even if the metering devices are not re-cycled inside the inhaler.

The metering devices in the series may be of such sizes and shapes as to allow delivery of different sized doses of the substance as the series is moved through the inhaler. For example, doses could be increased or decreased in volume over the length of the series, or otherwise varied in accordance with a course of treatment desired to be delivered by means of the inhaler.

Preferably, only one metering device of the series is presented to the inhalation passage at a time. Preferably, each time the indexing means is operated by a user, the metering device which has last transferred a dose of the substance to the inhalation passage is moved forward and replaced in the passage by the next metering device in the series. Thus, the metering devices are used one after another, and preferably not re-used after presentation to the inhalation passage.

Where the inhaler comprises a series of metering devices, these are preferably arranged together in the form of a flexible or semi-flexible chain. This chain may then be wound around itself inside the inhaler, allowing a relatively large number of metering devices to be stored inside the inhaler. The inhaler preferably comprises a metering device housing, in which the or each metering device may be housed prior to being presented to the storage chamber. A series of metering devices may be stored in the housing, used devices then conveniently being housed in a waste chamber in the inhaler.

Alternatively, the metering devices may be housed in the storage chamber itself, prior to their being moved via the outlet conduit to the inhalation passage.

The inhaler may comprise more than one series of metering devices, which series are moveable through the inhaler in parallel with one another. The indexing means of the inhaler would conveniently be operable to move a metering device in one series from its first to its second position, and at the same time a metering device in another series from *its* first to its second position, such that both metering devices are presented simultaneously to the inhalation passage. This inhaler may comprise more than one storage chamber to correspond to the respective more than one series of metering devices, such that each series delivers, in use, a different substance to the inhalation passage. Such an arrangement might be of use, for instance, in delivering two drugs which are to be administered together but which should be stored separately prior to administration. Alternatively, one of the series might be used to deliver a placebo and another a drug, relative amounts of the drug and placebo delivered being varied as the series are moved through the inhaler in use.

The metering devices are preferably joined together in the series, either permanently or releasably. They are preferably spaced at equal intervals along the length of the series, so as to transfer repeated doses of the same volume, although the devices may be spaced at intervals if it is desired to vary the volume of substance to be transferred by each device. In particular, however, the series is preferably continuous, in the sense that as the series passes through the outlet conduit, the only substance transferred with it is that trapped between the end elements of each successive device, there being no spaces between an end element of one device and the next end element of the next device in the series.

Each metering device of the series must have at least a first end element; the simplest form being a disc or flange having the same cross-sectional size and shape as that of the outlet conduit. Doses of the substance to be delivered are thus carried between the end elements of adjacent devices in the series. However, the metering devices may comprise bodies of any desired size and shape, so as to define an appropriate dosage volume between two successive metering devices passing through the outlet conduit of the storage chamber. Effectively, the end elements act as "spacers" to define dose volumes as the series passes through the outlet conduit.

The shape of each metering device is preferably also such that, when air is drawn through the inhalation passage past a metering device present in the passage, substantially no part of the region of the metering device between its first and second end elements, which region defines the dose of the substance to be delivered, is sheltered from the air flow.

Thus, in the region of each device between end elements, as large a proportion as possible of the outer walls of the device should be parallel to the direction of air flow through the inhalation passage, when the metering device is presented to the inhalation passage in use.

The or each metering device, in an inhaler in accordance with the third aspect of the invention, may be, disposable after it has been moved away from the inhalation passage. Alternatively, once all the metering devices of a series of devices have been passed through the inhaler, the series may be removed, as a chain, cleaned and inserted back into the metering device housing. The storage chamber of the inhaler, would then be re-loaded with a fresh supply of the substance to be delivered, and the inhaler operated in the usual way to achieve movement of the cleaned metering devices through the inhaler, via the storage chamber and outlet conduit to the inhalation passage.

Where the inhaler comprises a series of metering devices arranged in a chain-like conformation, it may also comprise cutting means by which individual metering devices, or groups of metering devices, may be severed from the series after passing through the outlet conduit. The individual devices or groups of devices are more easy to house in the inhaler after use. The cutting means may comprise any appropriate arrangement, eg, a cutting blade and anvil, preferably linked to the indexing means so as to sever a metering device of the series after that metering device has passed through the outlet conduit.

The inhalation passage of the inhaler is preferably so shaped that a dose of the substance to be delivered, transferred to the inhalation passage by means of the metering device, is subjected to substantially the entire air flow through the inhalation passage when air is drawn in via the air intake means. In this way, whether air is drawn into the inhaler through a single opening or several openings, the air flow through the inhaler is such that all of the air flows along a single duct at the point where the metering device is presented to the inhalation passage. This helps to ensure that the entire dose of the substance is removed from the metering device when a user inhales via the air intake means. The air intake means may comprise, for instance, a mouthpiece, so that a user may suck air into the inhaler using his mouth. Alternatively, it may comprise a fitting capable of being inserted into the nostril, allowing a user to inhale from the inhaler through his nose. A baffle, of an appropriate size and shape, may be included within the mouthpiece or other fitting. This, together with the contours of the inhalation passage itself, assists in breaking up the substance to be delivered and mixing it with air flowing through the passage.

The indexing means of the inhaler may comprise a ratchetlike mechanism, which allows the passage of metering devices in a series through the outlet conduit and into the inhalation passage, say, one at a time. This will then allow each metering device a "stepped" movement, rather than continuous movement, from its first to its second position and subsequently away from the inhalation passage.

For instance, the indexing means may comprise first engaging means for engaging a first metering device in the series and conveying it to its next position; and biasing means for subsequently urging the first engaging means back into engagement with a second metering device in the series, thus releasing the first device for subsequent passage through the inhaler. A second engaging means preferably engages the series of metering devices following release of the first metering device by the first engaging means, so that the series is fixed in position whilst the first engaging means moves back into engagement with the second metering device. The engaging means will need to be appropriately shaped to interact with the metering devices, preferably in such a way that substance is not released from a metering device, during its movement through the inhaler, until that device is in a position to present its dose of substance to the inhalation passage.

The indexing means is preferably operable by pushing down a single button or handle on the inhaler to cause appropriate movement of the indexing means. For instance, such a button or handle might be connected to a piston moveable within the inhaler, which piston comprises at least the first engaging means of the indexing means. Preferably, the indexing means is linked to the operation of any cutting means in the inhaler, so that a single action by the user causes drug delivery, indexing and severance of the next used metering device.

In use, the storage chamber of the inhaler is preferably positioned above the inhalation passage, which in turn is positioned above any waste chamber included in the inhaler. The metering device is thus moved downwardly through the inhaler in normal use, and the substance to be delivered flows downwardly with it through the outlet conduit.

The inhaler may comprise a body made up of two separate components, the body defining the storage chamber, inhalation passage, air intake means and, where applicable, the waste chamber and the metering device housing. The two components of the body are conveniently arranged one at least partly inside the other and capable of a degree of telescopic movement relative to one another, with the inhaler comprising biasing means to urge the two components in a direction away from one another.

The internal construction of these body components, and the arrangement of the metering device(s) inside them, is preferably such that movement of the two components in a direction towards one another, against the action of the biasing means, releases the metering device(s) for movement from one position to the next. In this way, movement of the two components relative to one another constitutes operation of the indexing means of the inhaler. The biasing means (which may take the form of, for instance, a spring) will then urge the two components of the inhaler body away from one another again, to a "rest" position in which the metering device which has last been presented to the inhalation passage is "captured" in its second position until the next operation of the indexing means.

Preferably, one of the body components defines the storage chamber (and preferably also the metering device housing), the other a waste chamber. The inhalation passage is preferably defined inside that component which also defines the storage chamber.

An inhaler in accordance with the present invention may also include a moisture-absorbent material stored inside the storage chamber, together with the substance to be delivered, to ensure that the substance remains dry at all times.

The inhaler preferably includes display means, operable by the indexing means so as to display an item of information to a user. The display means may, for instance, comprise counter means for indicating to the user the number of times that a dose of the substance has been presented to the inhalation passage, and/or the number of metering devices still remaining to be so presented. Display means of this general type are already known for use in conventional inhalers.

The inhaler may additionally comprise a timer (eg, an electronic or mechanical timer) and associated control means for ensuring that the substance may only be transferred to the inhalation passage at a desired dosage rate and that the user is unable to inhale the substance more often than is medically desirable over a given time period. The control means may comprise locking means, by which the indexing means is prevented from further operation until a predetermined period of time has elapsed since its last operation.

According to a fifth aspect of the present invention there is provided a method for transferring a desired volumetric dose of a flowable substance from a storage chamber containing the substance to an outlet conduit communicating with the chamber, the method comprising the step of passing a metering device in accordance with the first aspect of the invention from the storage chamber into the outlet conduit so as to cause substance surrounding the device in the storage chamber to pass with the device into the conduit, in the space defined between the end elements of the device and the intervening section of the inner walls of the conduit, the shape and dimensions of the device relative to those of the outlet conduit being as described in accordance with the first aspect of the invention.

Such a method may involve the use of an inhaler in accordance with the third aspect of the invention, in which case the method may be used to transfer the substance from the storage chamber into the inhalation passage of the inhaler, via the outlet conduit.

A metering device according to the first aspect of the invention may in particular be used to transfer a desired volumetric dose of a substance from a supply to a receptacle in which that dose is to be stored, for instance for subsequent use. The receptacle may be part of, for instance, a container for carrying one or more doses of a medicament for subsequent administration to a patient. The receptacle or container may be for use in an inhaler.

Thus, according to a sixth aspect of the present invention, being an embodiment of the fifth aspect, there is provided a method for use in loading a receptacle with a desired volumetric dose of a flowable substance, the method comprising the steps of providing a storage chamber containing the substance and an associated outlet conduit communicating with the chamber, and passing from the storage chamber into the outlet conduit a metering device according to the first aspect of the invention, the shape and dimensions of the device relative to those of the outlet conduit being as described in accordance with the first aspect of the invention. In this way, substance enclosed between the first and second end elements of the metering device and the intervening section of the inner walls of the conduit, may be transferred to the receptacle when the metering device is passed into the receptacle from the outlet conduit.

Preferably, the receptacle is itself of such shape and dimensions (ie, typically in the form of a conduit passing through a body) that the metering device may pass into the receptacle and be located therein with its first and second end elements in sealing engagement with the inner walls of the receptacle. A dose of substance may then be enclosed in the receptacle, trapped by means of the metering device. The relative dimensions of the metering device and receptacle are preferably such that the device, once located in the receptacle, has a tendency to remain therein unless actively urged out of it. Thus, the receptacle and metering device together provide a sealed enclosure in which a metered dose of substance is or may be contained until such time as the device is urged fully or partially out of the receptacle (eg, pushed out) by appropriate means.

According to a seventh aspect of the present invention, there is provided a receptacle in combination with a metering device located therein, as described above, the space defined by the device and the inner walls of the receptacle having been loaded (preferably using the method of the sixth aspect of the invention) with a desired volumetric dose of a flowable substance. The combination may be used to store and transport the dose of substance prior to its use.

The receptacle may form part of a container including a plurality of such receptacles, in each of which a desired dose of a desired substance may be held. Preferably, each receptacle in the container includes a metering device located inside the receptacle and is loaded with the desired flowable substance. The container may be adapted for use, for instance, in an inhaler, each dose of substance contained in its receptacles being presented to the inhalation passage of the inhaler at an appropriate point during use. Thus, the container may be in the form of a drug-carrying "magazine" or cartridge.

According to an eighth aspect, the invention provides a container including a plurality of receptacle-metering device combinations in accordance with the seventh aspect, as described above.

In the method according to the sixth aspect of the invention, the receptacle is preferably placed adjacent the outlet conduit in such a way that one forms a continuation of the other and the substance and metering device are able to pass from the outlet conduit into the receptacle without the possibility of escape of the substance into the atmosphere. Once the metering device has been passed fully into the receptacle, the latter may be removed from its position adjacent the outlet conduit.

Alternatively, the receptacle may itself serve as the outlet conduit, communicating directly with the storage chamber, if it is of appropriate dimensions relative to the metering device that the desired volume of space is defined between the end elements of the device and the intervening section of the inner walls of the receptacle as the device is passed from the storage chamber into the receptacle.

For use in a method according to the fifth aspect of the invention, the metering device may comprise a body in the form of an appropriately shaped spool. However, the method preferably involves passing through the storage chamber a plurality of metering devices in accordance with the fourth aspect of the invention, each device transferring as it is passed from the chamber into the outlet conduit its own metered dose of substance. Preferably, in the method according to the sixth aspect, each device is passed to a separate respective receptacle, for instance in a container comprising several receptacles, so as to load each of the receptacles in turn with a desired dose of the substance.

Thus, such a method may comprise the steps of moving into position adjacent the outlet conduit a first receptacle in a series of receptacles; transferring a dose of the substance to the first receptacle by passing a first metering device from the storage chamber into the first receptacle; replacing the first receptacle with a second receptacle in the series of receptacles; and transferring a dose of the substance to the second receptacle by passing a second metering device (for instance, in a series of such devices) from the storage chamber into the second receptacle. These steps may be repeated as often as desired.

Preferably, each metering device of a series of devices passed through the storage chamber is separated from the next device in the series after the former has been passed out of the storage chamber. The product of such a method is a receptacle containing a single metering device and a dose of substance transferred with that device, the combination of receptacle and device being in accordance with the seventh aspect of the invention.

According to a ninth aspect of the invention there is provided an inhaler for delivering a substance in a finely divided form, the inhaler comprising air intake means by which air may be drawn into the inhaler from the atmosphere; an inhalation passage communicating with the air intake means, through which passage air may be drawn using the air intake means; a receptacle and metering device in combination in accordance with the seventh aspect of the invention; indexing means operable to move the receptacle into a position in or adjacent the inhalation passage; and means for urging the metering device at least partially out of the receptacle so as to release into the inhalation passage the dose of substance contained in the receptacle between the end elements of the metering device, when the receptacle occupies its position in or adjacent the inhalation passage.

This inhaler preferably comprises a plurality of such preloaded receptacle-metering device combinations, the receptacles forming part of a larger container. The container may comprise, for instance, a cartridge (conveniently circular) adapted for rotation inside the inhaler, by the indexing means, so that each receptacle may be positioned in turn in or adjacent the inhalation passage. Alternatively, the container may be in the form of a chain of receptacles arranged together in a series and adapted for linear movement through the inhaler.

The means for urging the metering device out of the receptacle may comprise, for instance, a plunger operable in association with the indexing means to push the metering device out of the receptacle.

BRIEF DESCRIPTION OF THE DRAWING FIGURES

The present invention will now be described, by way of example only, with reference to the accompanying illustrative drawings, of which:

FIG. 5 shows in enlarged perspective view part of the series of metering devices shown in FIG. 4;

FIG. 6 shows in perspective view part of an alternative series of metering devices for use in the inhaler of FIGS. 1–3;

FIG. 11A is an elevational cross-sectional view of the inhaler of FIG. 9A, showing the piston as including upper flexible legs for preventing a double dosage; FIG. 11B;

FIG. 11B is a partial, elevational cross-sectional view of the inhaler of FIG. 11A showing the piston of the inhaler in its "at rest" position;

FIG. 11C is a partial, elevational cross-sectional view of the inhaler of FIG. 11A showing the piston of the inhaler when pressed downward by a user;

FIG. 9B is a longitudinal cross-sectional view of the inhaler of FIG. 19 during operation;

DETAILED DESCRIPTION OF THE DRAWINGS

The invention is described firstly by reference to inhalers in accordance with the third aspect, which incorporate metering devices in accordance with the first aspect.

Figure 1:
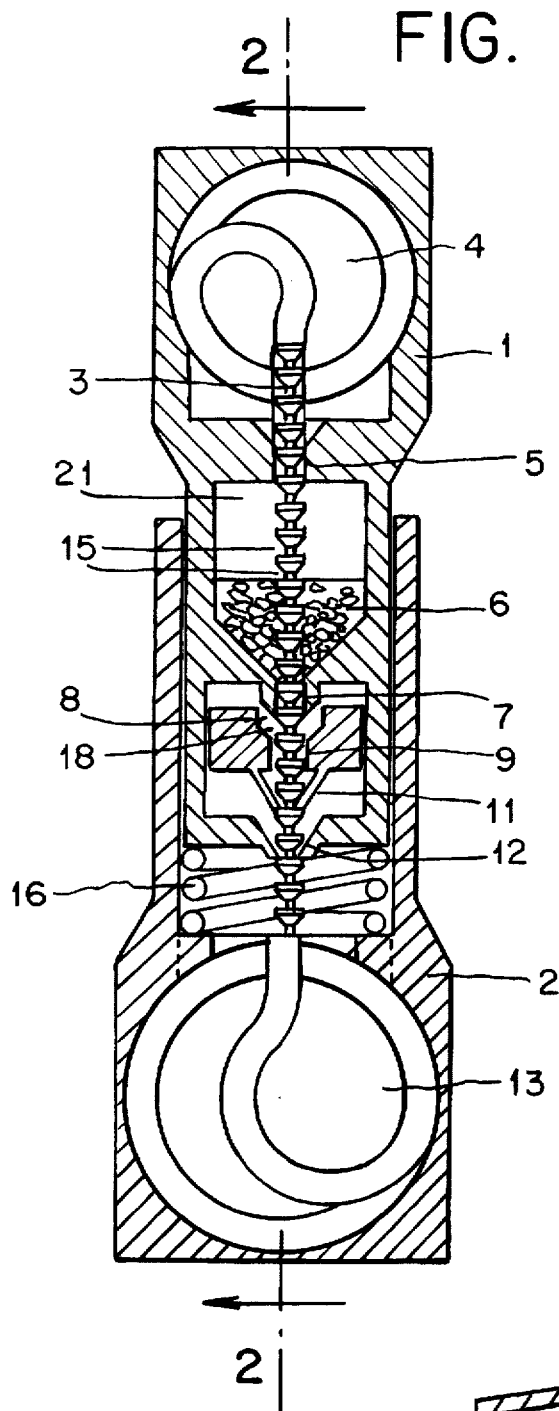
FIG. 1 is a longitudinal cross-section taken through an inhaler in accordance with the third aspect of the present invention.

Referring firstly to FIG. 1, the body of the inhaler shown comprises two components, 1 and 2, arranged one partly inside the other and capable of a degree of telescopic movement relative to one another. Component 1 is urged in a direction away from component 2 by the action of spring 16 located within component 2 (here shown in its fully extended conformation).

Figure 2:
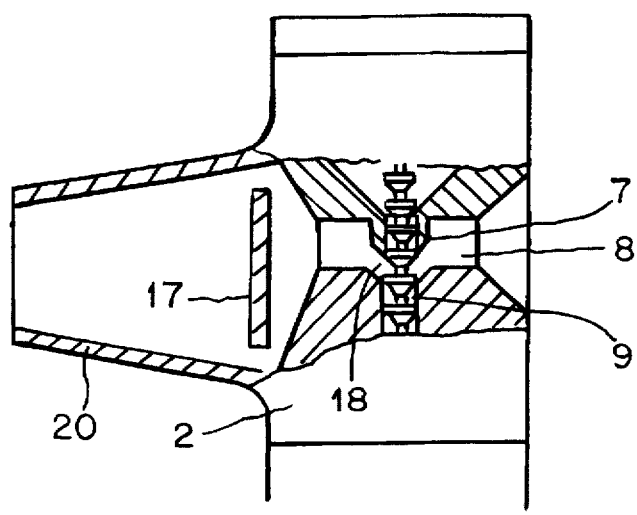
FIG. 2 is part of a section taken along the line II—II in FIG. 1, in the region of the inhalation passage.

Component 2 is provided with a mouthpiece 20, seen in the part section shown in FIG. 2. Through mouthpiece 20, a user is able to draw air into the inhaler and through the inhalation passage 8. Air enters the inhaler through an appropriately positioned inlet in the body of the inhaler (not shown as such in the Figures).

Component 2 is also connected to a set of pawls 11.

Inside component 1, there is defined a metering device housing 4 and a storage chamber 21, as well as the inner part of inhalation passage 8. The component has an associated set of pawls 12.

Inside storage chamber 21 is stored a quantity of the substance 6 to be delivered to a user via the inhaler. This might be, for example, a medicament, and will typically be in a dry, finely powdered form. A suitable dessicant may also be stored in chamber 21, to keep substance 6 dry.

Running through the inhaler is a flexible chain 3 of metering devices. The chain is coiled round on itself and stored in housing 4, and then passes downwardly through the inhaler, through opening 5, the storage chamber 21, channel 7, the inhalation passage 8, the opening 9, two sets of pawls 11 and 12 and thence into the waste chamber 13 defined in body component 2. In waste chamber 13, the free end of chain 3 is once more coiled round upon itself for economy of storage space.

Each metering device of the chain 3 comprises a solid metering body 15 having an upper edge ("end element") 15a. These bodies are of such a size and shape that, when two successive metering devices in the chain pass through the storage chamber outlet channel 7, the space defined between the end elements of the two devices and the internal wall of channel 7 is of the desired volume to define a dose of substance 6 to be delivered to a user of the inhaler. Each body 15 is thus dimensioned as to be able to pass through channel 7 with the outer edges of the end elements 15a flush with the internal wall of the channel, so as to prevent escape of substance 6 between each body and the internal wall.

Figure 4:
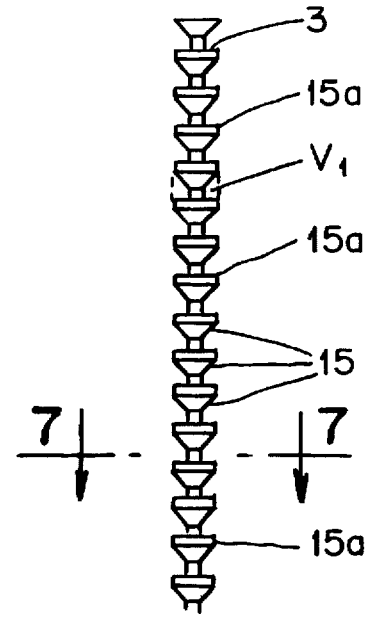
FIG. 4 shows in side view part of a series of metering devices, in accordance with the fourth aspect of the invention, for use in the inhaler of FIGS. 1–3.

The metering devices 15 are typically made from a moulded plastics material. A side view of part of chain 3 is shown in FIG. 4. An enlarged, perspective view of chain 3, having metering devices 15, is shown in FIG. 5. One dose of substance 6 is represented by volume $V_1$.

In FIG. 2, 17 is a baffle fitted inside mouthpiece 20. 18 is a conical recess positioned at the lower end of inhalation passage 8. The conical shape of this recess, complementing the shape of the metering devices and sloping downwardly, ensures that a metering device passing through it carries waste powder downwardly with it and away from the inhalation passage 8, preventing subsequent overdosing.

The inhaler shown in FIGS. 1–3 might typically be used as follows.

The inhaler would normally be supplied as a sealed unit, storage chamber 21 being pre-filled with an appropriate quantity of a medicament or other substance to be delivered, 6. This substance would be in the form of a dry, finely divided powder.

The inhaler would also be pre-loaded with a chain 3 of metering devices 15, stored inside housing 4 and projecting downwardly through chamber 21 and inhalation passage 8, with its free end engaged by pawls 11 and 12.

In use, the inhaler is held vertically upright, i.e. in the orientation as depicted in FIG. 1. Substance 6 then "floods" around the metering devices 15 in storage chamber 21, such that as two successive metering devices in the chain pass down through channel 7, the space between their end elements is packed with a predetermined quantity (volume $V_1$) of the substance. Thus, each metering device passing into inhalation passage 8 through channel 7 will also have passed through chamber 21 and received a dose of substance 6.

To release this dose, the user sucks air into the inhaler via mouthpiece 20. The air passes through the inhalation passage 8, collecting the dose of substance 6 from between the metering device 15 currently positioned in the inhalation passage and the next metering device in the chain. The air then passes out of the mouthpiece past baffle 17, which encourages breakup of substance 6 and its mixing with the air flow.

The inhalation passage 8 is internally contoured such that the substance 6 held by a metering device inside the passage is subjected to substantially the entire air flow through the passage and into the mouthpiece 20. Accordingly, the air flow through the passage 8 is along a single duct at the point where metering device 15 is presented to the air flow. All of the substance 6 should thus be removed from the metering device by the air flow.

To operate the inhaler so as to move the chain of metering devices through the inhalation passage 8, the procedure is as follows. Upper body component 1 is depressed in a direction towards lower body component 2, against the action of spring 16 (see FIG. 3), such that one further metering device 15 of chain 3 is pushed through the pawls 11 which are connected to lower component 2. When the user releases upper component 1, spring 16 urges this component away from lower component 2. Chain 3 now remains fixed in position relative to component 2, being gripped by pawls 11, but moves downwardly by one metering device through pawls 12, which are connected to component 1. Pawls 11 and 12 then engage with the undersides of the next metering devices in the chain 3. Spring 16 is thereby allowed to return to its decompressed length (as in FIG. 1).

Repeated operation of the inhaler in this way causes the chain 3 to progress in a stepwise manner from the upper to the lower component, one metering device 15 passing through inhalation passage 8 at a time. In effect, the two sets of pawls 11 and 12 act together, hand-over-hand, to move the chain 3 as one might pull a rope. Each depression of component 1 places a new metering device 15 in position in passage 8. A user can then inhale through mouthpiece 20 to release the dose of substance 6 transferred by the metering device. Subsequent depression of component 1 moves the now discharged metering device out of passage 8 towards opening 9, and the next metering device in the chain passes into passage 8, carrying a fresh dose of substance 6.

The discharged metering devices are moved downwardly, in this ratchet-like manner, into waste chamber 13. They are not re-presented to storage chamber 21 for re-use.

If the user fails to inhale a dose of substance 6 after operating the inhaler, that dose should fall into the conical recess 18, from whence subsequent operation of the inhaler will cause it to be carried through opening 9 and into waste chamber 13.

In one embodiment of the invention, means (not shown in the figures, but for instance an electrically operated drive means) may be provided to assist the user in effecting movement of the chain 3 through the inhaler, against the resistance provided by spring 16 and pawls 11 and 12.

Figure 3:
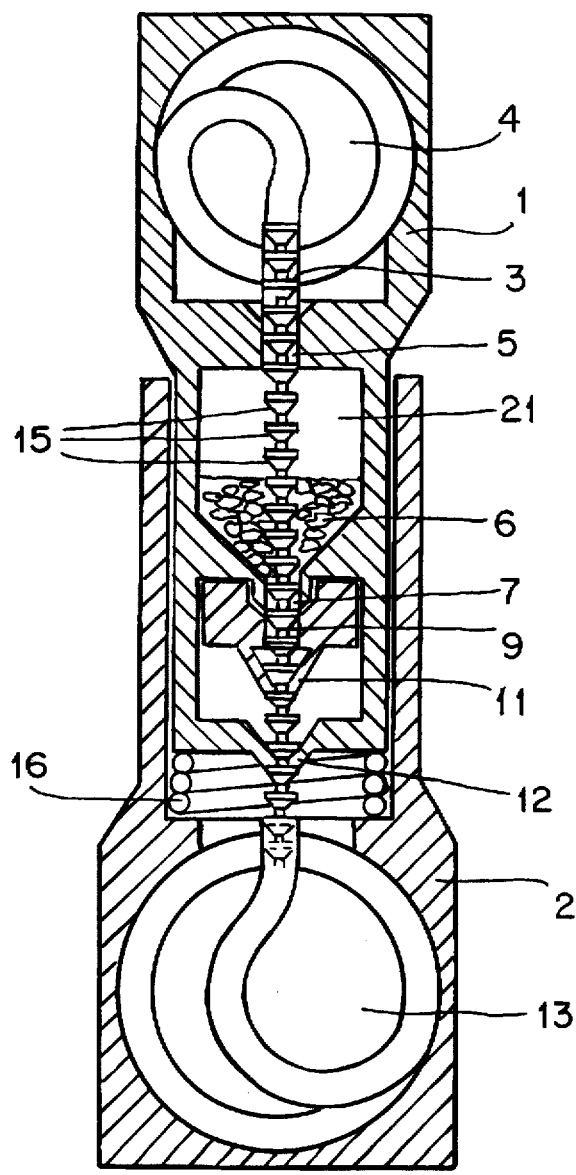
FIG. 3 is a longitudinal cross-section taken through the inhaler of FIGS. 1 and 2, in an alternative operating position.

For the inhaler of FIGS. 1–3, it is intended that when the entire length of the metering device chain 3 has passed through the inhalation passage 8, the complete inhaler, including enclosed metering devices, is discarded.

An alternative, and often preferred, type of metering device, for use in the inhaler of FIGS. 1–3, is shown in perspective view in FIG. 6. In this case, chain 30 is made up of metering devices 31, each being a solid body with an upper end element 32, again of such a size and shape that a desired volumetric dose, $V_2$, of substance 6 can be retained between two successive devices in the chain as they pass through channel 7 of the inhaler.

Each metering device 31 has an upper, disc-like portion 32 (the end element), of diameter such that its outer edges sit flush with the inner wall of channel 7. It also has a lower, narrower portion 33, having straight sides parallel to the longitudinal axis of chain 30. Such a straight-sided portion means that air flow past the metering devices in inhalation passage 8 is more likely to dislodge all of the dose of substance 6 held between two adjacent metering devices 31 and being presented to the inhalation passage. There is no region of volume $V_2$ which is "sheltered" from the air flow, as there might be in the case of the metering devices 15 shown in FIGS. 4 and 5.

Figure 7:
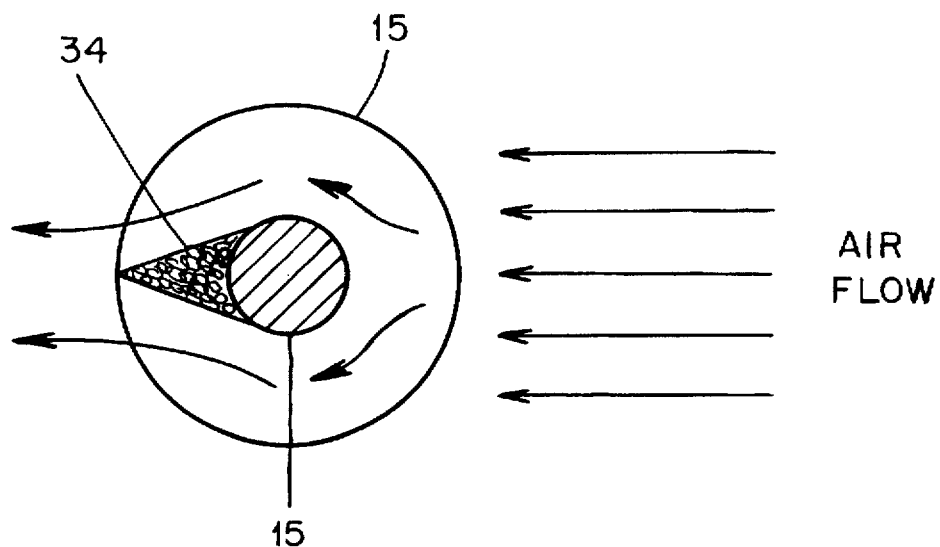
FIGS. 7 and 8 illustrate the air flow around metering devices as shown in FIGS. 5 and 6 respectively, when in use in an inhaler in accordance with the third aspect of the invention.
Figure 8:
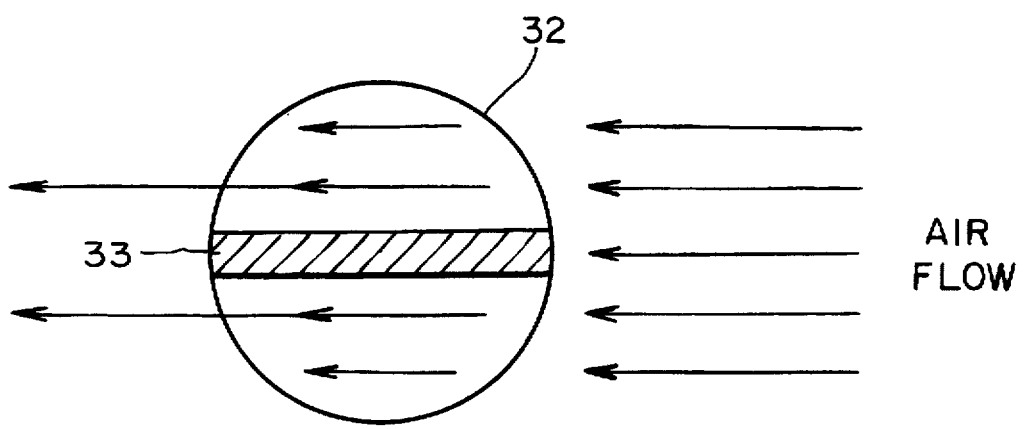

This is illustrated more clearly in FIGS. 7 and 8. FIG. 7 shows a section taken along the line VII—VII in FIG. 4, and illustrates how air would flow past the metering device 15 when the device was presented to the inhalation passage and a user inhaled through mouthpiece 20. Most of the dose of substance 6, held between the metering device and the next device in the chain, and defined as the two devices passed through channel 7, would be dislodged by the air flow and pass to the user. However, an area 34 would be sheltered from the air flow and substance 6 could remain lodged around the metering device, resulting in an underdose to the user.

The corresponding situation for metering devices 31, of FIG. 6, is shown in FIG. 8. Here, there is no area sheltered from the air flow and all of a dose of substance 6 presented to the inhalation passage is likely to be dislodged and delivered to the user. Naturally, the devices 31 must be positioned in use such that the sides of the narrower portions 33 are parallel to the normal direction of air flow through the inhalation passage 8.

Metering devices 31 are also easier to produce than are devices 15.

FIGS. 9A, 9B, 10B, 9A, 9B, 10A, 10B, 11A, 11B and 11C show inhalers in accordance with the third aspect of the invention which incorporate cutting means for severing individual metering devices from a chain after use, for ease of storage of the discarded devices.

Figure 9A:
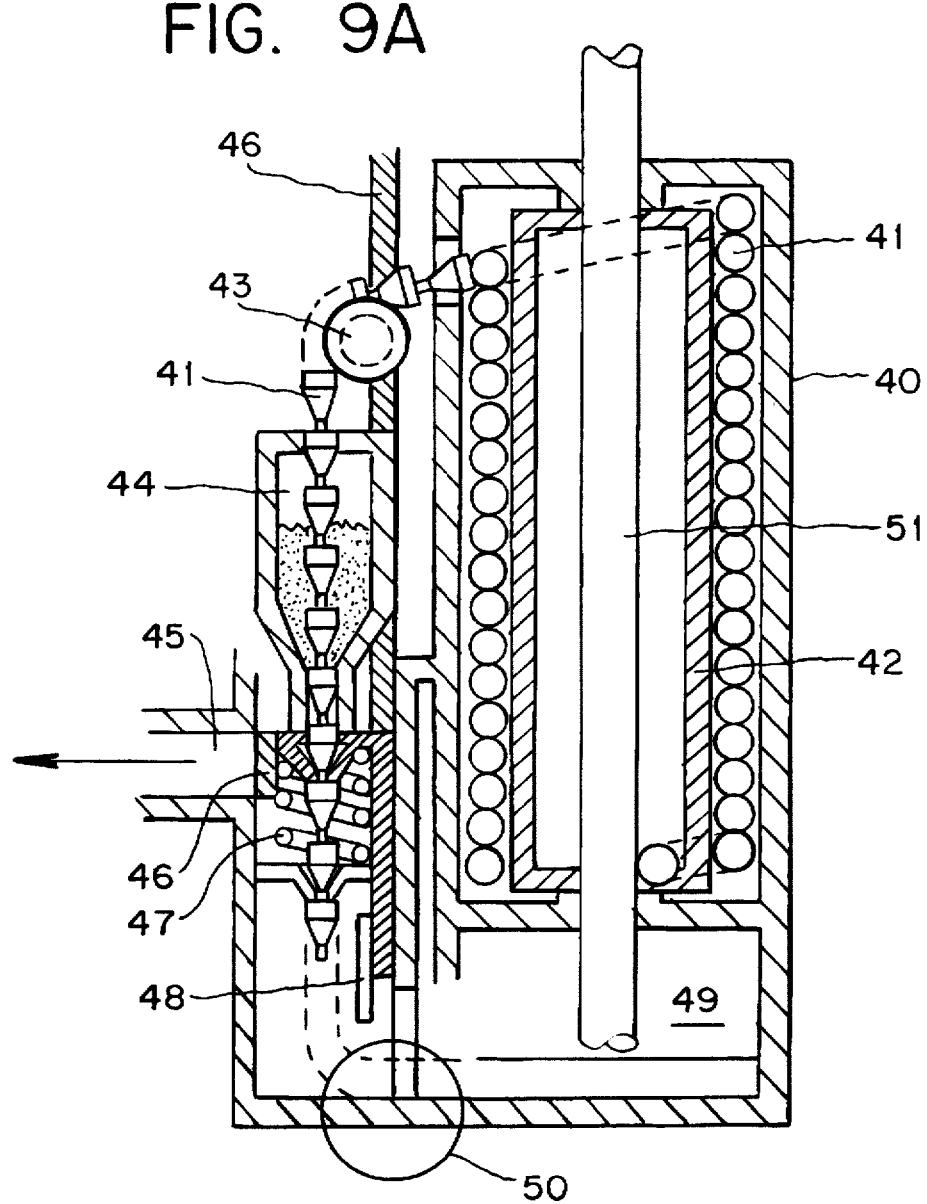
FIG. 9A is a longitudinal cross-sectional view of an inhaler according to a third aspect invention, which incorporates cutting means for severing individual metering devices from a chain after use.
Figure 9B:
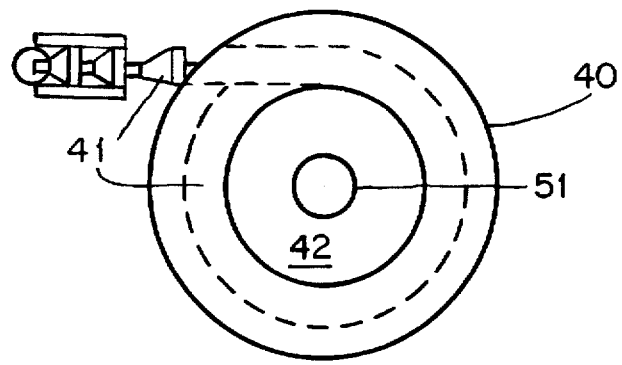
FIG. 9B is a transverse, cross-sectional view of the preferred embodiment of the inhaler illustrated in FIG. 9A.

The inhaler shown in FIG. 9 (in longitudinal cross-section in FIGS. 9A and 9B and transverse cross-section in FIG. 9B) comprises a metering device housing 40, in which a chain 41 of metering devices is wound spirally around a central cylindrical core 42, as shown, ready for use. Core 42 is able to rotate about axle 51. Chain 41 passes over a roller 43 through drug storage chamber 44 and then into inhalation passage 45, movement of lower devices in the chain being drawn by piston 46 acting against spring 47, in a similar manner to that in which the inhaler of FIGS. 1 and 3 functions. At its upper end, piston 46 is connected to a push button control (not shown) operable by the user to index metering devices through the inhaler. At its lower end, the piston is fixed to a blade 48.

Each time the user presses the push button down, the chain of metering devices moves downwards through the inhaler by one device. The blade 48 also moves downwards, severing one more metering device from the end of the chain 41 as it passes below the blade. The severed metering devices are stored in waste chamber 49.

Circle 50 indicates where an anvil might be positioned, against which blade 48 would rest in each cutting movement.

Figure 10B:
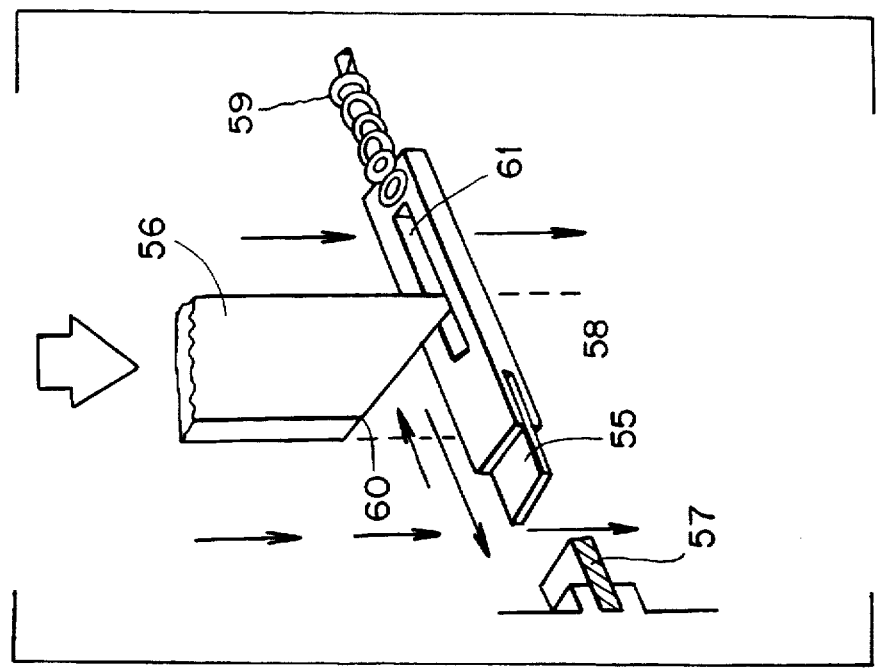
FIG. 10B is a partial prospective view of the inhaler of FIG. 10A showing downward movement of the piston during operation of the inhaler.

In the inhaler shown in FIG. 10A, a horizontal blade 55 is mounted below piston 56, opposite an anvil 57 (in the form of a metal insert in the side wall of the inhaler). FIG. 10B shows how movement of the piston 56 downwards (operated by a push button control, as is piston 46 in FIG. 9A) causes blade 55, mounted in a slide 58, to move out and strike the anvil. The slide 58 is pushed in this direction, against the action of spring 59, because of the interaction between the shaped lower portion 60 of the piston 56 and slot 61 in the slide 58. The slide is mounted within the inhaler casing.

Figure 10A:
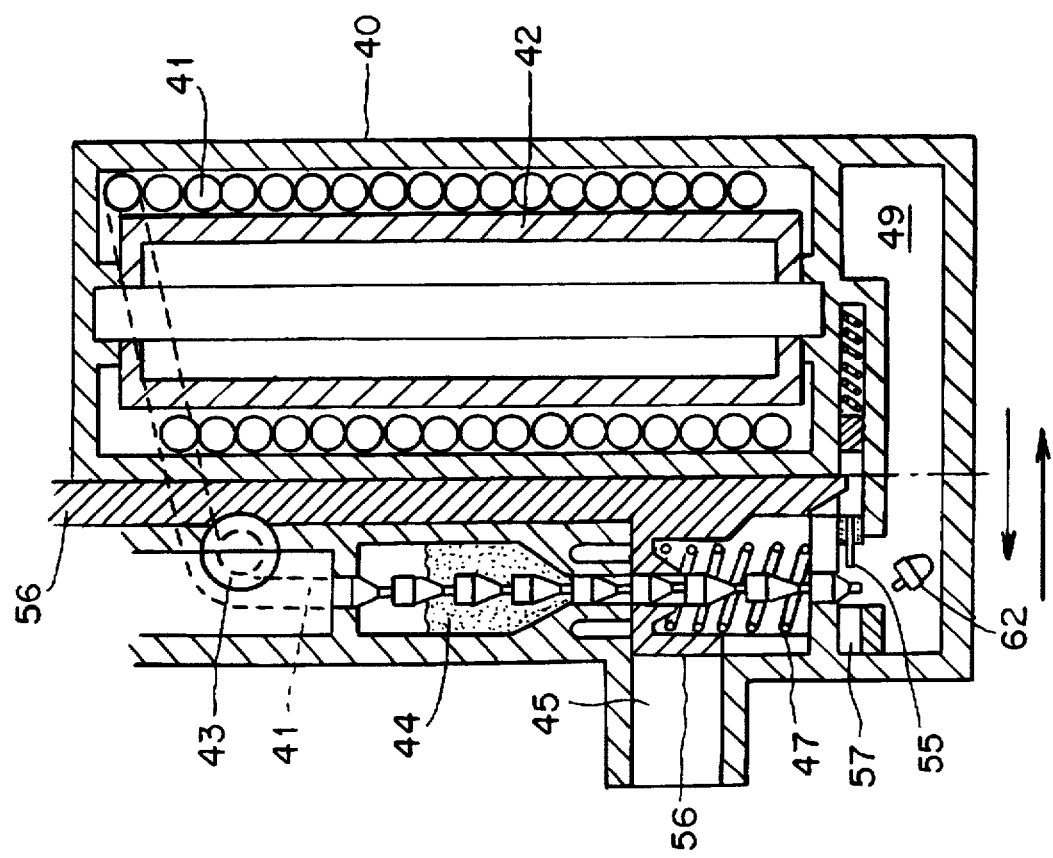
FIG. 10A is an elevational cross-sectional view of the inhaler of FIG. 9A, showing a horizontal blade thereof mounted below a piston prior to operation.

Severed metering devices such as 62 are stored in waste chamber 49, as seen in FIG. 10A. Other structural and operational features of the FIG. 10 inhaler are the same as those of the FIGS. 9A, 9B and 9C inhaler.

In another similar inhaler, part of which is shown in FIG. 11A, two horizontally oriented blades 66 are mounted in a piston 67, the two flexible legs 68 of which when pushed downwardly by the user flex inwardly due to the presence of rollers 69. As the blades 66 come together, a metering device is cut from the end of chain 41 and falls to waste into chamber 49.

Operation of the piston 67 is shown in FIG. 11B, the top drawing showing the piston in its "at rest" position and the bottom drawing the piston when pressed down by the user.

Note that in the FIGS. 11A, 11B and 11C inhaler, the piston 67 comprises upper flexible legs 70 to prevent the chain 41 from pulling back and effecting a double dose. This in turn allows a reduction in the space below the inhaler mouthpiece 71, labelled x in FIG. 11A. Because of this, a spring performing an equivalent function to spring 47 in FIGS. 9A, 9B and 9C must be positioned elsewhere in the inhaler other than cavity 72 (eg. directly below the user-operated push button, not seen in FIG. 11A).

In the inhalers of FIGS. 9A, 9B, 10A, 10B, 11A, 11B, and 11C a single operation of the push button effects not only dose delivery, but also reindexing of the metering devices and their severance for storage in waste chamber 49.

It can also be seen in the inhalers of FIGS. 9A, 9B, 10A, 10B, 11A, 11B, 11C that the relevant parts of the pistons 46, 56 and 67 are level with the metering devices that they convey into the inhalation passages, so that in each case the metering device and piston move downwardly *together*. This prevents any powder, from the metering device being conveyed, from falling to waste during movement of the metering device from the drug storage chamber to the inhalation passage.

Figure 12A:
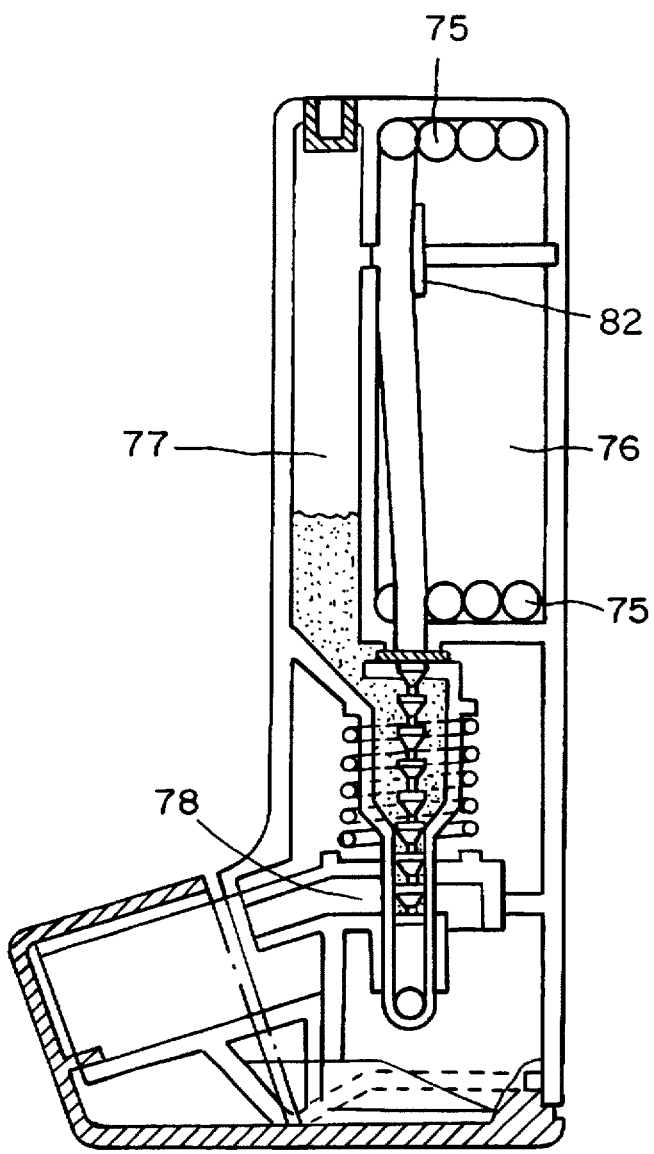
FIG. 12A is a side, longitudinal cross-sectional view of an inhaler according to the invention having a series of metering devices stored therein.
Figure 12B:
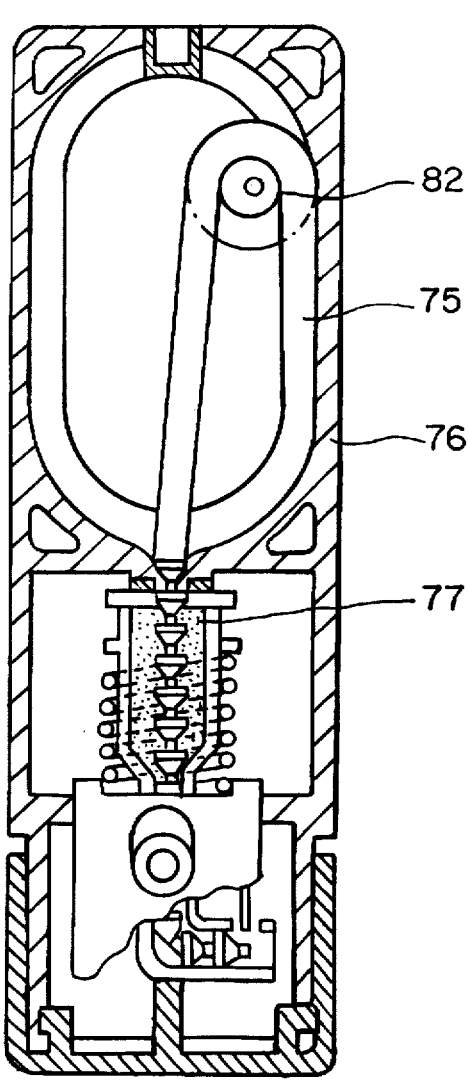
FIG. 12B is a front, longitudinal cross-sectional view of the preferred embodiment of inhaler illustrated in FIG. 12A.

FIGS. 12A and 12B shows how a chain 75 of metering devices may be stored in an inhaler according to the invention, in a housing 76 located adjacent the drug storage chamber 77 and above the inhalation passage 78. Parts only of the inhaler are shown, schematically, in FIG. 12, by means of longitudinal cross-sections viewed from the side (FIG. 12A) and from the front (FIG. 12B).

The chain 75 is wound spirally around a cylindrical core which may have lugs on its outer surface for accurate location of the chain. The core is able to rotate about a central axle to allow the chain to unwind in a controlled fashion over a freewheeling roller 82, as the metering devices are pulled through the inhaler by indexing means (not shown).

Figure 13:
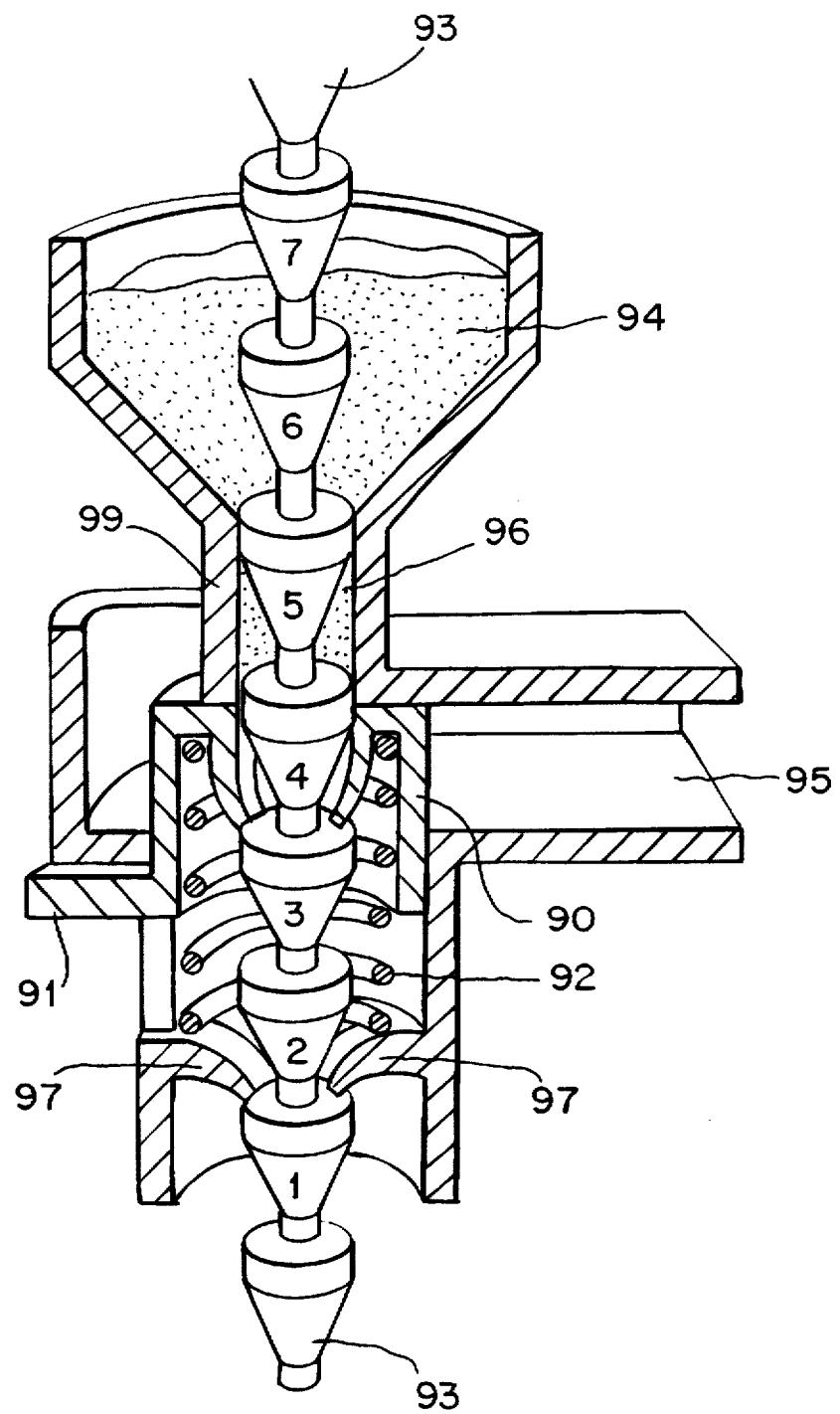
FIG. 13 is a partial, longitudinal cross-sectional view of a further preferred embodiment of the inhaler of the present invention showing indexing means at its "at rest" position.
Figure 14:
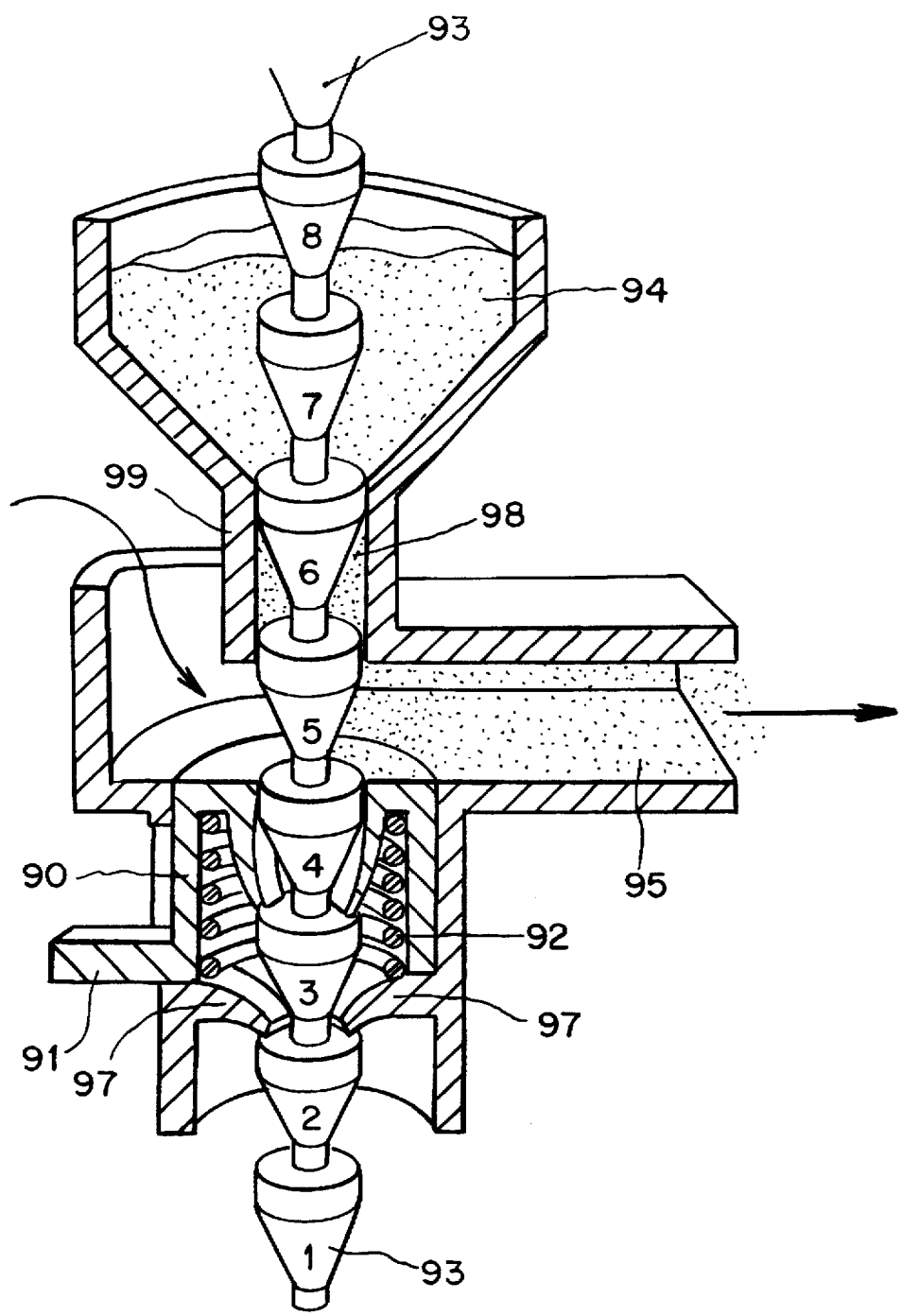
FIG. 14 is a partial, longitudinal cross-sectional view of a preferred embodiment of FIG. 13, showing present invention showing indexing means during activation by a user.

FIGS. 13 and 14 show an inhaler which incorporates a preferred form of indexing means consisting primarily of a piston 90 (manually operated by means of a handle 91 protruding through the side wall of the inhaler) and a spring 92. A chain 93 of metering devices (sequentially numbered, for clarity) is shown passing through drug storage chamber 94, its outlet conduit 99 and inhalation passage 95.

FIG. 13 shows the indexing means in its "at rest" position. A dose of powder, 96, is held in readiness for delivery between metering devices 4 and 5 and the inner walls of outlet conduit 99. Piston 90 is held in position by the upward action of spring 92.

When the user wishes to release the dose of powder 96, he does so by pushing handle 91 downwardly, against the action of spring 92 (FIG. 14). Piston 90 moves down, its legs carrying chain 93 with it, and the dose 96 is released into the inhalation passage 95, as shown, as the user inhales (the user must continue to hold the handle 91 down as he inhales). The direction of air flow is indicated by the arrows.

When the user releases handle 91, piston 90 returns to its "at rest" position under the action of spring 92, but chain 93 is prevented from returning by the legs 97 of the inhaler body. A fresh dose 98 is now trapped between metering devices 5 and 6 in the outlet conduit 99, and the inhaler is ready for re-use.

One particular use for an inhaler according to the third aspect of the present invention, to provide a programmed dose variation, might be as follows. In some therapies it is desirable to vary the dose of drug delivered to a recipient from a dry powder inhaler during a course of treatment. A typical example of this is a course of treatment for individuals wishing to give up smoking cigarettes. Here the principal difficulty is the smoker's addiction to nicotine inhaled in cigarette smoke. It is believed that the addiction can be overcome by taking a course of nicotine that reduces the smoker's craving by gradually reducing the amount of nicotine absorbed over a controlled period of time.

A number of products are currently available which purport to do this, one such product being an adhesive patch containing a nicotine formulation which is placed on the body so that the nicotine may be absorbed into the blood stream through the skin. Patches are placed on the body at regular intervals, usually every 24 hours, and over a period of time (typically three months) the size of the patch or strength of formulation is reduced to zero.

There are a number of problems with this approach, but it is believed that the principle drawback is that the rate of nicotine absorption into the blood stream is slow and varies between recipients.

The perceived benefit of smoking is that nicotine enters the blood stream almost immediately the smoke is inhaled. Delivering a nicotine formula directly to the lungs by inhalation may give a similar immediate effect. However, the drawbacks to the use of inhalers (dry powder or aerosol type) of designs presently available are two fold:

1. the current designs generally deliver a consistent amount of formulation on each operation of the device;
2. there is no feature that limits the number of deliveries over a time span.

An inhaler in accordance with the present invention may be used to overcome either or both of these drawbacks.

By altering the dimensions and shape of each metering device of a series, the volume of substance transferred by that device can be altered. If this alteration takes place progressively from one end of the series of metering devices to the other, the volume of substance carried, and hence the amount the patient inhales, can be progressively altered. In the circumstances of a dose of nicotine formulation, discussed above, this would mean making the volume of substance progressively smaller as the series passes through the inhaler in use.

Figure 15:
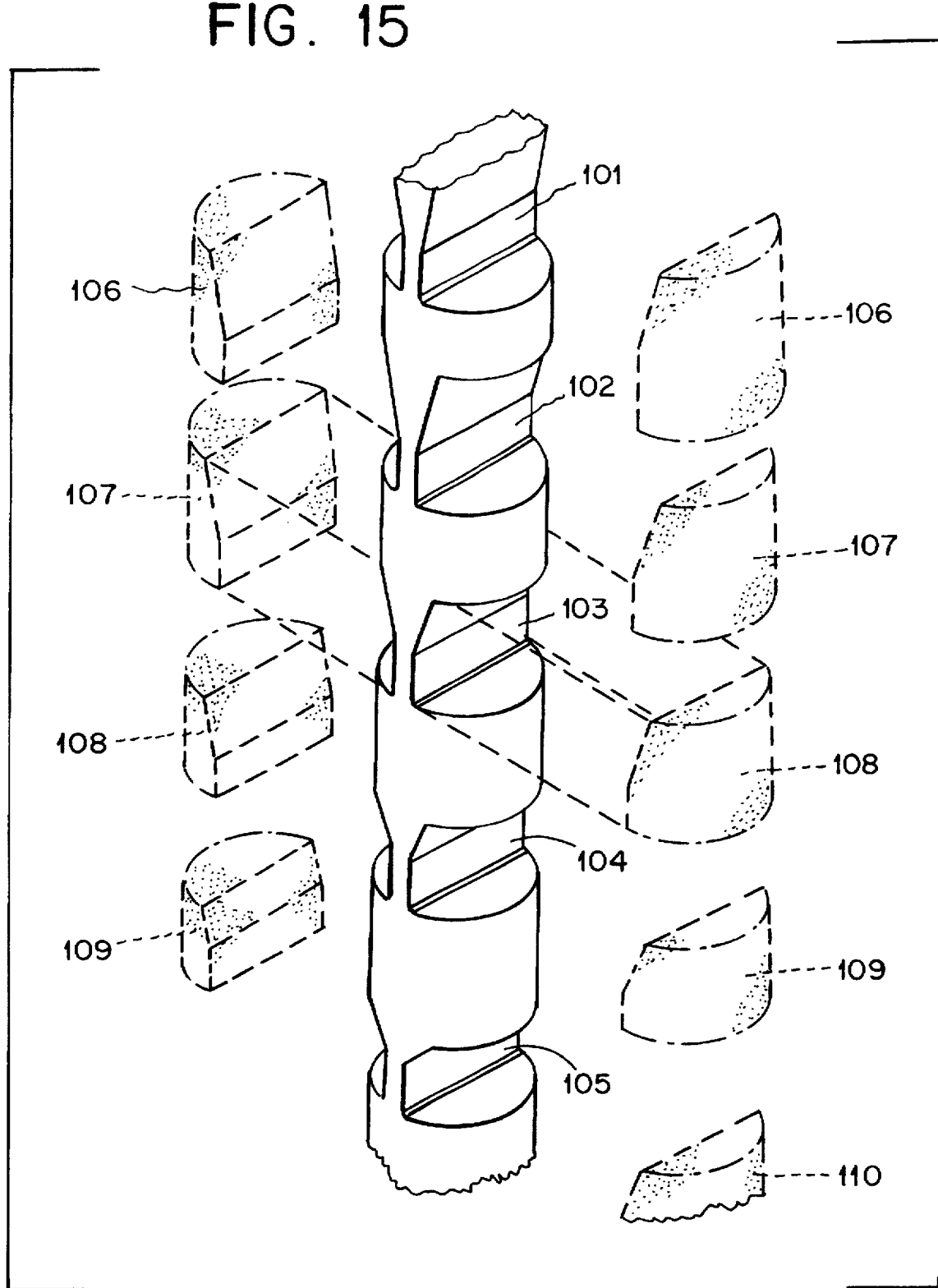
FIG. 15 shows in perspective view a series of metering devices in accordance with the invention, for use in an inhaler for delivering varying doses of a drug.

An example of such a series of metering devices is shown in FIG. 15, in which successive devices 101–105 are shaped so as to carry progressively (in this case) smaller doses 106–110 of a substance to be delivered. Such a chain of metering devices could be used, for example, in any of the inhalers shown in FIGS. 1–3 or 9–12. The chain effectively incorporates a "programme" of dose deliveries.

In practice, it may be found that at some stage in a course of treatment the volume of substance delivered becomes too small for the user to taste/sense, if the substance is flavoured for example. If this proves to be the case, an inhaler having two flexible chains of metering devices indexed in parallel could be constructed, one chain (a) passing through a storage chamber containing a drug formulation and the second chain (b) passing through a second chamber containing a placebo. The chain (a) would be arranged to dispense a maximum amount of drug at the beginning of a course of treatment and a minimum amount of drug at the end of the chain; the chain (b) would be arranged to dispense a minimum amount of placebo at the beginning and a maximum amount of placebo at the end of the chain. Thus, with the metering devices indexing in parallel through the inhaler, the total volume dispensed from a pair of metering devices on each inhalation remains consistent throughout the life of the inhaler.

This arrangement could also be used in circumstances requiring the dispensing of two type of drugs that may not be suitable for storing in one chamber.

In order to overcome the potential problem of a user inhaling more frequently than is desirable, the inhaler may be fitted with a timing mechanism. This could comprise a simple light, an electrically operated flag or a mechanically operated flag operated by a clockwork mechanism, or a more sophisticated electronic timing device operating a lock mechanism.

Figure 16:
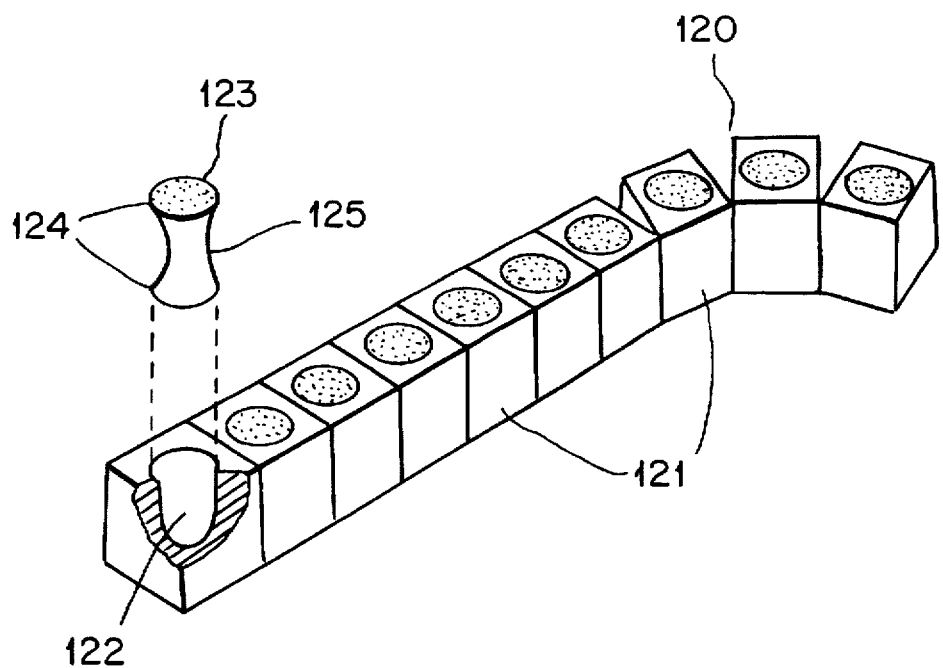
FIG. 16 is a perspective view of drug-carrying container in the form of a bandolier in accordance with a further preferred embodiment of the present invention.
Figure 17:
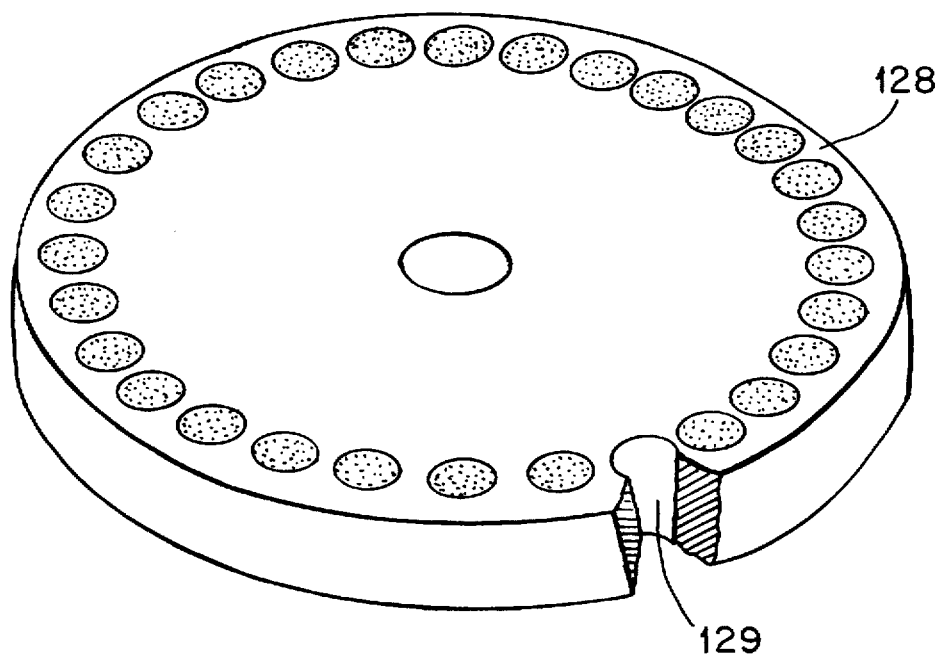
FIG. 17 is a perspective view of drug-carrying container in the form of a disc in accordance with a further preferred embodiment of the present invention.

FIGS. 16 and 17 are perspective views of drug-carrying containers in accordance with the eighth aspect of the invention. Each container comprises a plurality of receptacles in accordance with the seventh aspect of the invention, in each of which receptacles a desired volumetric dose of a substance, in this case a drug, is held. The two containers are for use in an inhaler in accordance with the ninth aspect of the invention.

The container 120 shown in FIG. 16 is in the form of a "bandolier" made up of a series of units 121. Each unit, or receptacle, 121 is in the form of a cuboid body having an open-ended cylindrical conduit 122 running through it. A metering device 123, in the form of a spool, is located inside each conduit 122. Each spool 123 has upper and lower flanges 124 and a narrower neck portion 125. The flanges (end elements) 124 are a tight but slidable fit inside the conduit 122 and the overall length of the spool 123 is more or less the same as the overall length of the conduit 122.

When the bandolier 120 is ready for use in an inhaler, each conduit 122 contains one spool such as 123, and is filled with a powdered drug which occupies the space defined between the flanges 124, the neck portion 125 and the inner walls of the conduit 122. The spool 123 and the conduit 122 are of such dimensions that this space is of the precise volume of the dose of drug to be delivered in use. Because the flanges 124 are a tight fit inside conduit 122, they provide seals at the open ends of the conduit, to prevent escape of the drug contained in it. The spools may, however, be pushed out of either of the open ends of the conduits by suitable means provided in the inhaler, at the time when the dose of drug contained in the conduit is to be delivered to the user.

The container 128 shown in FIG. 17 is in the form of a disc which carries around its periphery a series of conduits 129 similar to conduits 122 shown in FIG. 16. When the container is ready for use, each conduit 129 contains a metering device of similar form to spool 123 shown in FIG. 16, with a desired quantity of drug trapped between the outer flanges of the metering device and the inner walls of the conduit 129. Each of the conduits in the container thus contains one dose of the drug, each to be delivered to a user in turn when the container is used in an inhaler. The doses may be of the same or differing amounts in the conduits of the container; if they are of differing amounts, this may be achieved by using metering devices of differing shapes and sizes.

Figure 18:
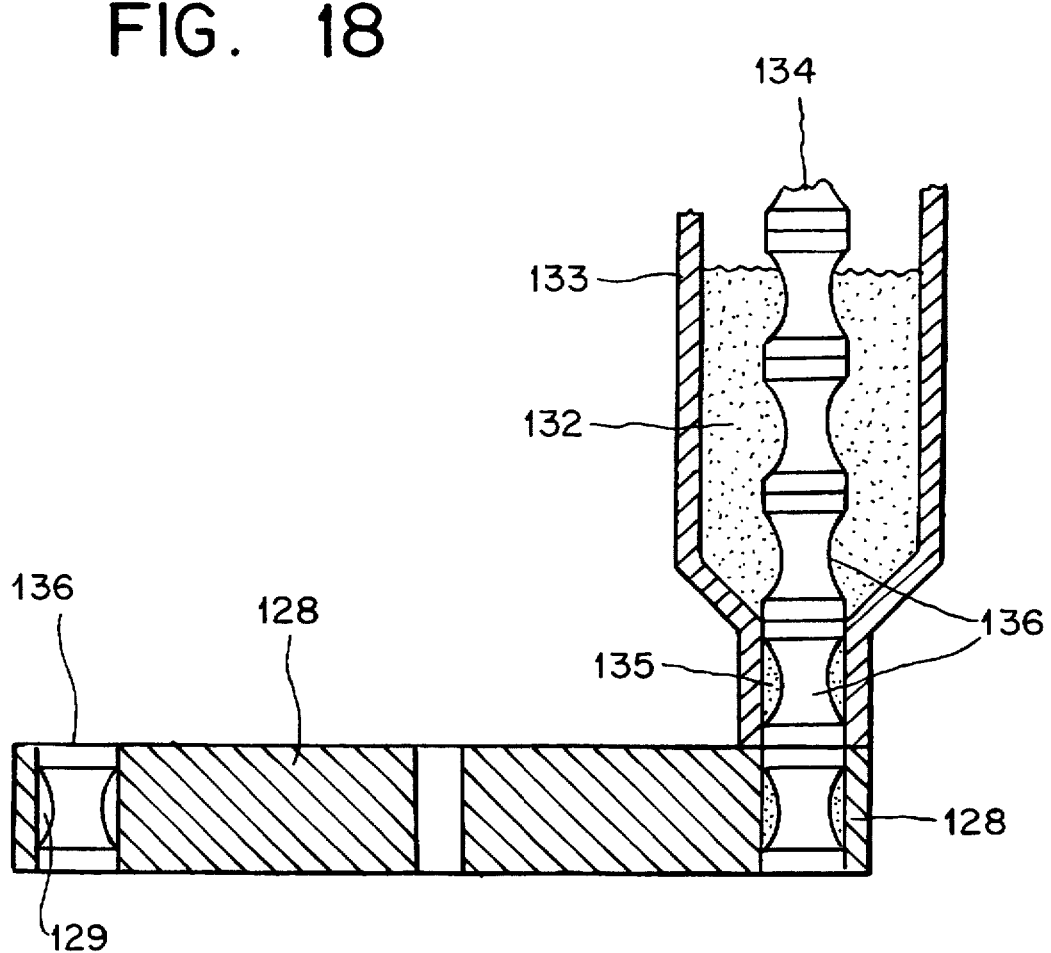
FIG. 18 shows, by means of a cross-section taken through suitable apparatus, how the container of FIG. 17 may be loaded with a drug.

FIG. 18 shows schematically how the container 128 of FIG. 17 may be loaded with a drug prior to use in an inhaler. The method being used is in accordance with the sixth aspect of the present intention, and would be equally applicable to loading a container such as 120 shown in FIG. 16.

A supply of the desired drug 132 is contained in storage chamber 133. A chain of metering devices (spools) 134 is arranged to run downwardly through the storage chamber 133 and its outlet conduit 135. The container 128 is positioned so that one of its conduits 129 sits directly below the outlet conduit 135.

The drug 132 in chamber 133 "floods" around the spools 136 in chain 134. The chain is moved downwardly by appropriate means (not shown in FIG. 18) so that the next spool at the lower end of the chain is pushed firstly down through the outlet conduit 135 and then into conduit 129. The two conduits 135 and 129 are of the same dimensions. Thus, as a spool 136 enters outlet conduit 135, it carries with it the desired quantity of drug 132 in the space bound by its upper and lower flanges and the inner walls of the outlet conduit 135. This accurately defined dose of the drug is also transferred to conduit 129 in the container 128, as the chain 134 is moved further down and the spool enters the conduit 129.

By appropriate means (again not shown in FIG. 18), the container 128 is then rotated so that the next conduit 129 moves into position below outlet conduit 135, and the chain 134 is moved downwardly once more by the length of one metering device 136. As this happens, the next device 136 in the chain enters the next conduit 129, again carrying with it the required dose of drug 132. In this way, by moving in a stepwise fashion both the conduits 129 and the chain 134 of metering devices, each of the conduits 129 in container 128 may be loaded with a spool 136 and a dose of drug 132 of an appropriate amount, ready for subsequent use of the container.

A number of storage chambers such as 133, each containing a different drug, may be appropriately mounted relative to the container being filled, so that different receptacles in the container may be filled with different drugs. If different receptacles are to contain different sized doses of a drug, the chain 134 should be made up of appropriately positioned metering devices of the necessary sizes and shapes.

Figure 19A:
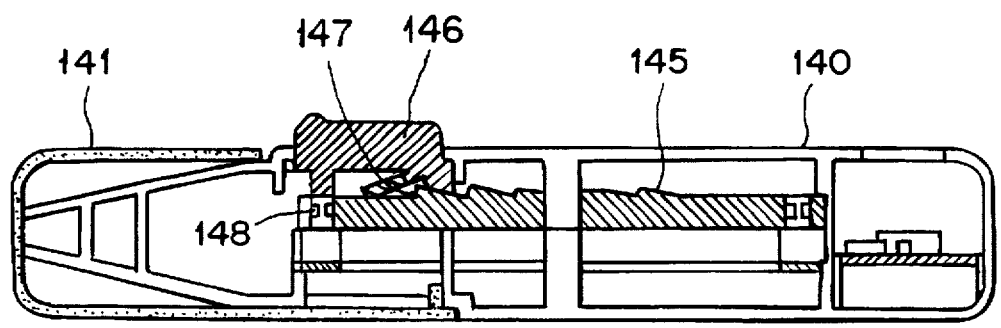
FIG. 19A is a longitudinal cross-sectional view of the preferred embodiment of the inhaler illustrated in FIG. 17.
Figure 19B:
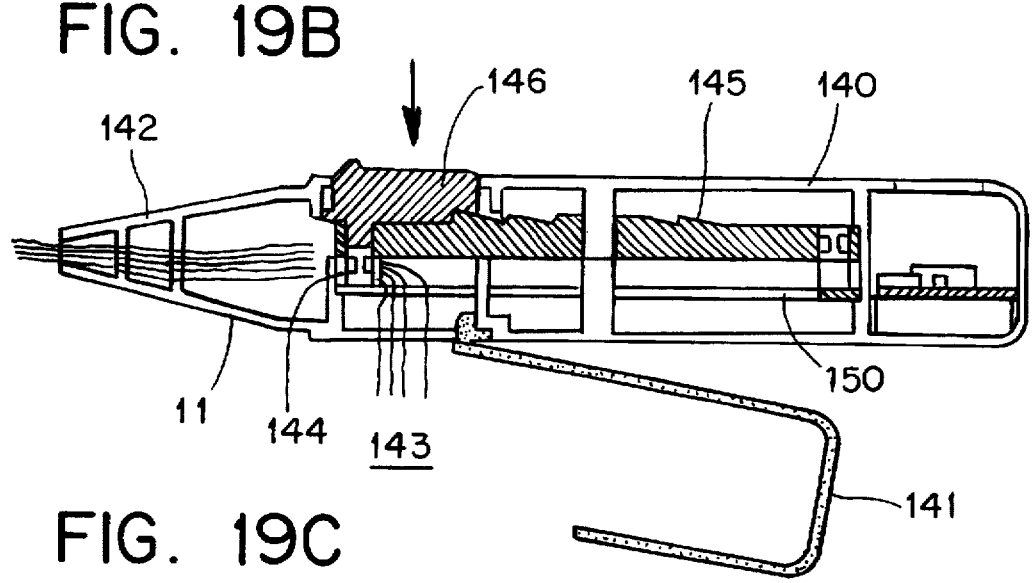
FIG. 19C is a longitudinal cross-sectional view of the inhaler of FIG. 19A following operation by a user.
Figure 19C:
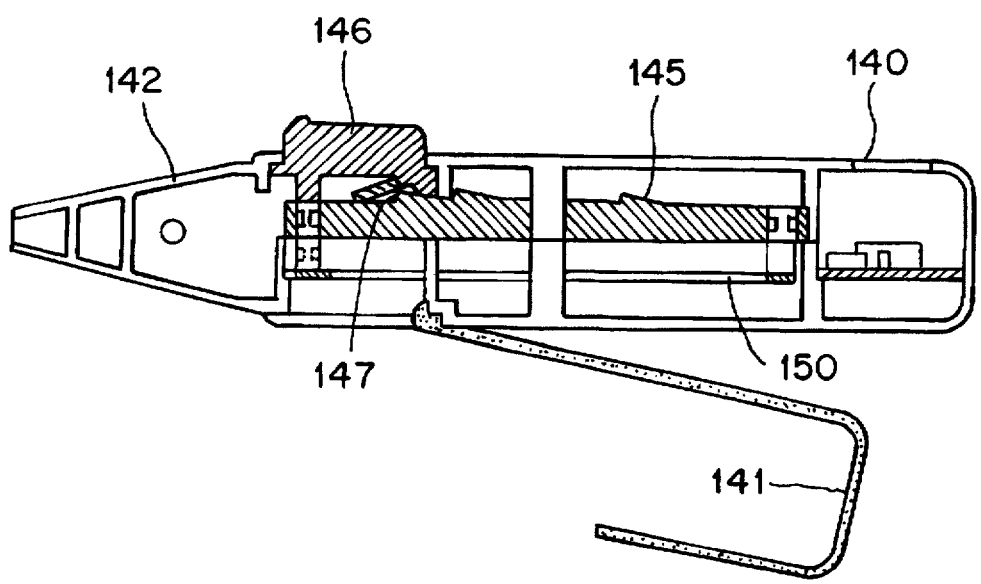

FIGS. 19A, 19B, and 19C shows an inhaler in accordance with the ninth aspect of the present invention, in various stages of its use. The exact construction of most parts of the inhaler 140 is not critical to the invention, although it can be seen that it comprises a cover 141 which is removed prior to use (FIGS. 19B and C) and a mouthpiece 142 through which the user may suck air which enters the inhaler as shown at 143 and passes through the inhalation passage 144.

The inhaler 140 contains a disc-like magazine 145, similar to the container shown in FIG. 17 and having a plurality of drug-carrying receptacles around its periphery. Suitable indexing means, including a push button 146 and a ratchet mechanism 147, engages with the upper surface of disc 145. As shown in FIG. 19B, depression of the push button 146 (as shown by the arrow) pushes spool 148 downwards and almost fully out of a first receptacle, positioned adjacent the inhalation passage 144, into the inhalation passage (FIG. 19B). As the spool 148 is pushed into the inhalation passage, it carries with it the measured quantity of drug which it has been used to contain inside the magazine 145. The user can then inhale through the mouthpiece 142 so as to take up the drug now released into the inhalation passage. The upper flange of the spool remains, however, held by the lower part of the receptacle.

When the user then releases push button 146, the ratchet mechanism 147 causes disc 145 to rotate by one step so that the next receptacle is brought into register with the inhalation passage 144. The inhaler is thus reset and ready for delivery of another dose of drug. The "empty" spool 148, not having been pushed fully out of the first receptacle, continues to move round with the first receptacle, supported by the lower guide 150.

In an inhaler such as that shown in FIGS. 19A, 19B, and 19C, the metering devices may alternatively be pushed upwardly towards an inhalation passage positioned above the drug-filled receptacles in use.

Figure 20:
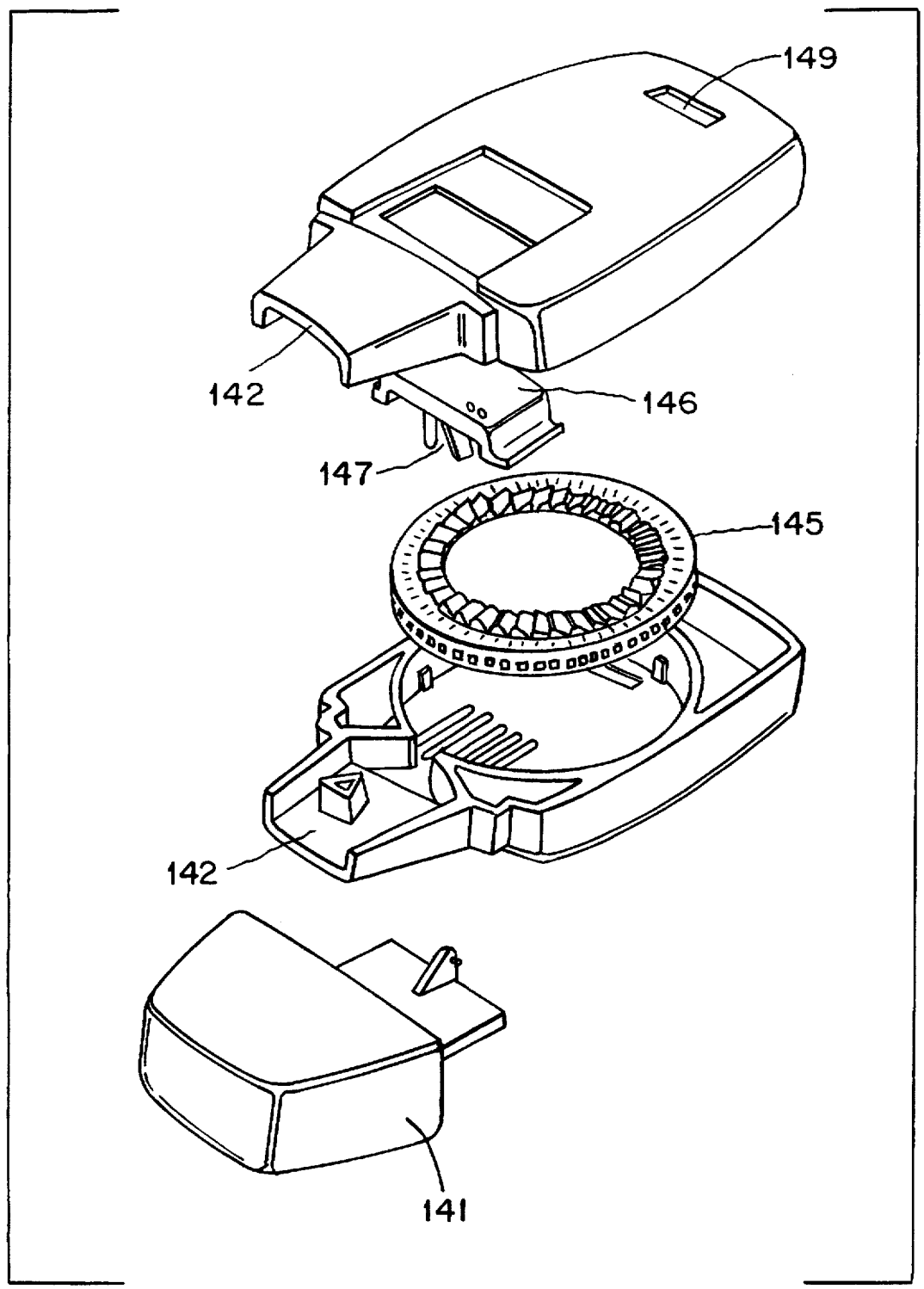
FIG. 20 is an exploded perspective view of the inhaler of FIG. 19.

FIG. 20 shows an exploded perspective view of the components of the inhaler 140 shown in FIG. 19. It can be seen that the upper surface of disc 145 is specially profiled so as to engage with the ratchet mechanism 147 provided on the underside of push button 146. The inhaler is also provided with conventional display means (not shown) for displaying to the user, through window 149, an indication of the number of doses already taken or alternatively of the number of doses remaining in magazine 145.

It will be understood that an inhaler such as that shown in FIGS. 19A, 19B, 19C and 20 is only one example of an inhaler according to the ninth aspect of the invention. Other examples, comprising different types of drug container, different ways of mounting the container, different types of indexing means, etc are also possible. The container may, for instance, take the form of a chain of receptacles such as the bandolier 120 shown in FIG. 16. Each receptacle in the container may carry more than one metering device, if necessary to increase the capacity of the container overall. The inhaler may be provided pre-loaded with a container carrying the required number of drug doses. The container may be removable and refillable or replaceable once empty.

The advantages of using a metering device in accordance with the present invention, particularly in a powder inhaler, are that the volume of substance transferred with each metering device can be accurately controlled. In a drug-carrying container in accordance with the invention, the type of substance carried may be different in each of its receptacles. In an inhaler in accordance with the third or ninth aspect of the invention, the use of a metering device in accordance with the first aspect ensures that the accurately defined dose of drug carried with the metering device is entirely transferred to the inhalation passage and may then be subjected to substantially all the air flow, thus reducing the risk of the user receiving an incorrect dosage.

I claim:

1. Apparatus for dispensing a plurality of desired volumetric doses of a flowable substance, comprising:

a storage chamber for a flowable substance;

an outlet conduit communicating with said storage chamber and having an inner surface;

an inhalation passage;

a series of metering devices, each of said metering devices including a first end element and a second end element having a perimeter adapted for a sealing engagement with the inner surface of said outlet conduit, and an intermediate portion, located between the first end element and the second end element, which is smaller in cross-section than the first end element and the second end element; and, means for advancing said metering devices in series for moving one of said metering devices between a position within said storage chamber, at which one of said metering devices is surrounded by the flowable substance, and a position within said outlet conduit, at which the perimeter of each of the first end element and the second end element forms a continuous seal with the inner surface of the outlet conduit, and the intermediate portion, the first end element, the second end element and the inner surface of said outlet conduit define between them an intermediate dosing space containing an amount of the flowable substance which surrounds said one of said metering devices within said storage chamber and passes with said one of said metering devices into said outlet conduit, said metering devices are arranged in a continuous series, so that as the continuous series passes through said outlet conduit, the only flowable substance transferred with it is trapped between said end elements of successive metering devices, there being no spaces between said end element of one of said metering devices and a successive end element of the next said metering device in the continuous series, and wherein said means for advancing said metering devices is operable for moving, on each operation, said metering device which has last transferred a dose of the flowable substance to the inhalation passage forward through the apparatus and to replace that said metering device in the inhalation passage by said metering device next in the series, such that only one of said metering devices is presented to the inhalation passage at a time.

2. Apparatus according to claim 1 in which the means for advancing the metering devices is adapted to maintain the metering devices substantially free from contact with the walls of the storage chamber while they are advanced through it.

3. Apparatus according to claim 1 in which the devices are attached to one another in a flexible or semi-flexible chain.

4. Apparatus according to claim 3 in which the first end element of one device in the series also serves as the second end element of the preceding device in the series, such that the desired volume is defined between two successive end elements as successive devices in the series pass through the outlet conduit.

5. Apparatus according to claim 3 in which the devices are arranged in a continuous series, such that as the series passes through the outlet conduit, the only substance transferred with it is that trapped between the end elements of successive devices, there being no spaces between an end element of one device and the next end element of the next device in the series.

6. Apparatus according to claim 5, wherein said metering devices are each of a size and shape for allowing delivery of different sized doses of the flowable substance as said metering devices are moved through the apparatus in series.

7. Apparatus according to claim 1, wherein said means for advancing said metering devices includes indexing means operable for moving each of said metering devices from a first position within said storage chamber to a second position in which a desired volumetric dose of the flowable substance is presented with said metering device to the inhalation passage.

8. Apparatus according to claim 7, wherein said indexing means comprises first engaging means for engaging a first metering device in the series of devices and conveying said first device to its next position, biasing means for subsequently urging said first engaging means back into engagement with a second of said metering devices in the series, thus releasing the first metering device for subsequent passage through the apparatus and second engaging means for engaging the series of metering devices following release of the first metering device by said first engaging means, so that the series is fixed in position while said first engaging means moves back into engagement with said second metering device.

9. Apparatus according to claim 7, wherein said indexing means is operable for moving each of said metering devices away from the inhalation passage after the device has reached its second position, so that said metering device is not re-presented to said storage chamber after having reached its second position.

10. Apparatus according to claim 7, wherein a shape of said, or each said, metering device is such that when air is drawn through the inhalation passage past one of said metering devices present in the inhalation passage, substantially no part of the region of said metering device between its first end element and its second end element is sheltered from the air flow.

11. Apparatus according to claim 7, wherein the inhalation passage is so shaped that a dose of the flowable substance to be delivered, transferred to the inhalation passage by means of said metering device, is subjected to substantially the entire air flow through the inhalation passage.

12. Apparatus according to claim 7, wherein said storage chamber is positioned above the inhalation passage so that each metering device is movable downwards through the apparatus, the flowable substance to be delivered flowing downwards with said metering device through said outlet conduit.

13. Apparatus according to claim 1, further comprising a metering device housing in which said metering devices are able to be housed prior to being presented to said storage chamber.

14. Apparatus for dispensing a plurality of desired volumetric doses of a flowable substance, comprising:

a storage chamber for a flowable substance;

an outlet conduit communicating with said storage chamber and having an inner surface;

an inhalation passage;

a series of metering devices, each of said metering devices including a first end element and a second end element having a perimeter adapted for a sealing engagement with the inner surface of said outlet conduit, and an intermediate portion, located between the first end element and the second end element, which is smaller in cross-section than the first end element and the second end element; and, means for advancing said metering devices in series for moving one of said metering devices between a position within said storage chamber, at which one of said metering devices is surrounded by the flowable substance, and a position within said outlet conduit, at which the perimeter of each of the first end element and the second end element forms a continuous seal with the inner surface of the outlet conduit, and the intermediate portion, the first end element, the second end element and the inner surface of said outlet conduit define between them an intermediate dosing space containing an amount of the flowable substance which surrounds said one of said metering devices within said storage chamber and passes with said one of said metering devices into said outlet conduit, said means for advancing said metering devices includes indexing means operable for moving each of said metering devices from a first position within said storage chamber to a second position in which a desired volumetric dose of the flowable substance is presented with said metering device to the inhalation passage, said indexing means further comprising:

first engaging means for engaging a first metering device in the series of devices and conveying said first device to its next position;

biasing means for subsequently urging said first engaging means back into engagement with a second of said metering devices in the series, thus releasing the first metering device for subsequent passage through the apparatus; and, second engaging means for engaging the series of metering devices following release of the first metering device by said first engaging means, so that the series is fixed in position while said first engaging means moves back into engagement with said second metering device.

15. Apparatus according to claim 14, wherein said indexing means is operable for moving each of said metering devices away from the inhalation passage after the device has reached its second position, so that said metering device is not re-presented to said storage chamber after having reached its second position.

16. Apparatus according to claim 14, wherein a shape of said, or each said, metering device is such that when air is drawn through the inhalation passage past one of said metering devices present in the inhalation passage, substantially no part of the region of said metering device between its first end element and its second end element is sheltered from the air flow.

17. Apparatus according to claim 14, wherein the inhalation passage is so shaped that a dose of the flowable substance to be delivered, transferred to the inhalation passage by means of said metering device, is subjected to substantially the entire air flow through the inhalation passage.

18. Apparatus according to claim 14, wherein said storage chamber is positioned above the inhalation passage so that each metering device is movable downwards through the apparatus, the flowable substance to be delivered flowing downwards with said metering device through said outlet conduit.

19. Apparatus according to claim 14, further comprising a metering device housing in which said metering devices are able to be housed prior to being presented to said storage chamber.

20. Apparatus according to claim 14, wherein said means for advancing said metering devices is adapted for maintaining said metering devices substantially free from contact with walls of said storage chamber while said metering devices are advanced through said storage chamber.

21. Apparatus according to claim 14, wherein said metering devices are attached to one another in a flexible or semi-flexible chain.

22. Apparatus for dispensing a plurality of desired volumetric doses of a flowable substance, comprising:

a storage chamber for a flowable substance;

an outlet conduit communicating with said storage chamber and having an inner surface;

an inhalation passage;

a series of metering devices, each of said metering devices including a first end element and a second end element having a perimeter adapted for a sealing engagement with the inner surface of said outlet conduit, and an intermediate portion, located between the first end element and the second end element, which is smaller in cross-section than the first end element and the second end element; and, means for advancing said metering devices in series for moving one of said metering devices between a position within said storage chamber, at which one of said metering devices is surrounded by the flowable substance, and a position within said outlet conduit, at which the perimeter of each of the first end element and the second end element forms a continuous seal with the inner surface of the outlet conduit, and the intermediate portion, the first end element, the second end element and the inner surface of said outlet conduit define between them an intermediate dosing space containing an amount of the flowable substance which surrounds said one of said metering devices within said storage chamber and passes with said one of said metering devices into said outlet conduit, said means for advancing said metering devices includes indexing means operable for moving each of said metering devices from a first position within said storage chamber to a second position in which a desired volumetric dose of the flowable substance is presented with said metering device to the inhalation passage, said indexing means being operable for moving each of said metering devices away from the inhalation passage after the device has reached its second position, so that said metering device is not re-presented to said storage chamber after having reached its second position.

23. Apparatus according to claim 22, wherein a shape of said, or each said, metering device is such that when air is drawn through the inhalation passage past one of said metering devices present in the inhalation passage, substantially no part of the region of said metering device between its first end element and its second end element is sheltered from the air flow.

24. Apparatus according to claim 22, wherein the inhalation passage is so shaped that a dose of the flowable substance to be delivered, transferred to the inhalation passage by means of said metering device, is subjected to substantially the entire air flow through the inhalation passage.

25. Apparatus according to claim 22, wherein said storage chamber is positioned above the inhalation passage so that each metering device is movable downwards through the apparatus, the flowable substance to be delivered flowing downwards with said metering device through said outlet conduit.

26. Apparatus according to claim 22, further comprising a metering device housing in which said metering devices are able to be housed prior to being presented to said storage chamber.

27. Apparatus according to claim 22, wherein said means for advancing said metering devices is adapted for maintaining said metering devices substantially free from contact with walls of said storage chamber while said metering devices are advanced through said storage chamber.

28. Apparatus according to claim 22, wherein said metering devices are attached to one another in a flexible or semi-flexible chain.

29. Apparatus for dispensing a plurality of desired volumetric doses of a flowable substance, comprising:

a storage chamber for a flowable substance;

an outlet conduit communicating with said storage chamber and having an inner surface;

a series of metering devices, each of said metering devices including a first end element and a second end element having a perimeter adapted for a sealing engagement with the inner surface of said outlet conduit, and an intermediate portion, located between the first end element and the second end element, which is smaller in cross-section than the first end element and the second end element;

means for advancing said metering devices in series for moving one of said metering devices between a position within said storage chamber, at which one of said metering devices is surrounded by the flowable substance, and a position within said outlet conduit, at which the perimeter of each of the first end element and the second end element forms a continuous seal with the inner surface of the outlet conduit, and the intermediate portion, the first end element, the second end element and the inner surface of said outlet conduit define between them an intermediate dosing space containing an amount of the flowable substance which surrounds said one of said metering devices within said storage chamber and passes with said one of said metering devices into said outlet conduit; and, a metering device housing in which said metering devices are able to be housed prior to being presented to said storage chamber.

30. Apparatus according to claim 29, further comprising an inhalation passage, wherein said means for advancing the metering devices includes indexing means operable for moving each of said metering devices from a first position within said storage chamber to a second position in which a desired volumetric dose of the flowable substance is presented with said metering device to the inhalation passage.

31. Apparatus according to claim 30, wherein said indexing means is operable for moving each of said metering devices away from the inhalation passage after the device has reached its second position, so that said metering device is not re-presented to said storage chamber after having reached its second position.

32. Apparatus according to claim 30, wherein a shape of said, or each said, metering device is such that when air is drawn through the inhalation passage past one of said metering devices present in the inhalation passage, substantially no part of the region of said metering device between its first end element and its second end element is sheltered from the air flow.

33. Apparatus according to claim 30, wherein the inhalation passage is so shaped that a dose of the flowable substance to be delivered, transferred to the inhalation passage by means of said metering device, is subjected to substantially the entire air flow through the inhalation passage.

34. Apparatus according to claim 30, wherein said storage chamber is positioned above the inhalation passage so that each metering device is movable downwards through the apparatus, the flowable substance to be delivered flowing downwards with said metering device through said outlet conduit.

35. Apparatus according to claim 30, wherein said means for advancing said metering devices is adapted for maintaining said metering devices substantially free from contact with walls of said storage chamber while said metering devices are advanced through said storage chamber.

36. Apparatus according to claim 29, wherein said metering devices are attached to one another in a flexible or semi-flexible chain.

37. Apparatus for dispensing a plurality of desired volumetric doses of a flowable substance, comprising:

a storage chamber for a flowable substance;

an outlet conduit communicating with said storage chamber and having an inner surface;

a series of metering devices, each of said metering devices including a first end element and a second end element having a perimeter adapted for a sealing engagement with the inner surface of said outlet conduit, and an intermediate portion, located between the first end element and the second end element, which is smaller in cross-section than the first end element and the second end element, said metering devices being attached to one another in a flexible or semi-flexible chain; and, means for advancing said metering devices in a continuous series for moving one of said metering devices between a position within said storage chamber, at which one of said metering devices is surrounded by the flowable substance, and a position within said outlet conduit, at which the perimeter of each of the first end element and the second end element forms a continuous seal with the inner surface of the outlet conduit, and the intermediate portion, the first end element, the second end element and the inner surface of said outlet conduit define between them an intermediate dosing space containing an amount of the flowable substance which surrounds said one of said metering devices within said storage chamber and passes with said one of said metering devices into said outlet conduit, so that as the continuous series of said metering devices passes through said outlet conduit, the only flowable substance transferred with the continuous series of said metering devices is that which is trapped between the first end element and the second end element of successive said metering devices, there being no spaces between an end element of one of said metering devices and an adjacent end element of a next said metering device in said continuous series, said metering devices each being of a size and shape for allowing delivery of different sized doses of the flowable substance as said metering devices are moved through said apparatus in said continuous series.

* * * * *